(12) United States Patent
Conde-Frieboes et al.

(10) Patent No.: US 7,517,854 B2
(45) Date of Patent: Apr. 14, 2009

(54) MELANOCORTIN RECEPTOR AGONISTS

(75) Inventors: Kilian Waldemar Conde-Frieboes, Måløv (DK); Ulrich Sensfuss, Copenhagen V (DK); Kjeld Madsen, Værløse (DK); Nils Langeland Johansen, Copenhagen Ø (DK); Leif Christensen, Roskilde (DK); Thomas Kruse Hansen, Herlev (DK); Birgitte Schjellerup Wulff, Virum (DK)

(73) Assignee: Novo Nordisk A/S, Bagsvaerd (DK)

( * ) Notice: Subject to any disclaimer, the term of this patent is extended or adjusted under 35 U.S.C. 154(b) by 377 days.

(21) Appl. No.: 11/278,014

(22) Filed: Mar. 30, 2006

(65) Prior Publication Data

US 2007/0027091 A1 Feb. 1, 2007

Related U.S. Application Data

(63) Continuation of application No. PCT/DK2004/000657, filed on Sep. 29, 2004.

(30) Foreign Application Priority Data

Sep. 30, 2003 (DK) .............................. 2003 01417

(51) Int. Cl.
*A61K 38/12* (2006.01)
(52) U.S. Cl. .......................... 514/11; 514/16; 530/317
(58) Field of Classification Search ........................ None
See application file for complete search history.

(56) References Cited

U.S. PATENT DOCUMENTS

| 4,457,864 A | 7/1984 | Hruby et al. |
| 5,731,408 A | 3/1998 | Hadley et al. |

FOREIGN PATENT DOCUMENTS

| EP | 292291 | 5/1987 |
| WO | 98/27113 | 6/1998 |
| WO | 99/54358 | 10/1999 |
| WO | 01/00224 | 1/2001 |
| WO | 02/18437 | 3/2002 |
| WO | 02/081443 | 10/2002 |
| WO | 03/007949 | 1/2003 |
| WO | 03/009850 | 2/2003 |
| WO | 2004/099246 | 11/2004 |

OTHER PUBLICATIONS

Benarek, 2000, Biochemical and Biophysical Research Communications, 272, 23-28.*
Benarek, 1999, Biochemical and Biophysical Research Communications, 261, 209-213.*
Vergoni, A.V. et al., Eur J Pharmacol., vol. 179, pp. 347-355 (1990).
Huszar, D. et al., Cell, vol. 88, pp. 131-141 (1997).
Kelbig, M.L. et al., Proc Natl Acad Sci USA, vol. 92, pp. 4728-4732 (1995).
Yeo et al., Nat Genet, vol. 20, pp. 111-112 (1998).
Vaisse et al., Nat Genet, vol. 20, pp. 113-114 (1998).
Grieco, P. et al., J Pept Res, vol. 62, pp. 199-206 (2003).
Cai et al., Peptides, pp. 892-895 (2001).
Hofmann, R.M. et al., Peptides, pp. 992-993 (2001).
Cheung, A.W. et al., Bioorg Med Chem Lett, vol. 13 (7), pp. 1307-1311 (2003).
Bednarek, M. et al., Biochem Biophys Res Commun, vol. 272 (1), pp. 23-28 (2000).
Bednarek, M. et al., Peptides, vol. 20 (3), pp. 401-409 (1999).
Holder, J.R. et al., J Med Chem, vol. 45 (13), pp. 2801-2810 (2002).
Grieco, P. et al., BioChemical and BioPhysical Research Communications, vol. 292(4), pp. 1075-1080 (2002).

* cited by examiner

*Primary Examiner*—Andrew D Kosar
*Assistant Examiner*—Satyanarayana R Gudibande
(74) *Attorney, Agent, or Firm*—Shelby J. Walker

(57) ABSTRACT

Small cyclic peptides of the formula X1-X2-X3-X4-X5-X6-X7-$R^1$ comprising 7-12 amino acid residues are provided. Said peptides are MC4 receptor agonists, and thus useful in the treatment of obesity and related diseases.

31 Claims, No Drawings

MELANOCORTIN RECEPTOR AGONISTS

CROSS-REFERENCE TO RELATED PATENT APPLICATIONS

This patent application is a continuation of co-pending International (PCT) application PCT/DK2004/000657, filed Sep. 29, 2004 (published as WO 2005/030797), which designates the United States, and which claims the benefit (under 35 USC § 119) of Danish Patent Application PA 2003 01417, filed Sep. 30, 2003, the entirety of each of which is hereby incorporated by reference.

SEQUENCE LISTING

In connection with this application, a Sequence Listing has been submitted. The submission, filed herewith, does not include any new matter and is comprised of three CD-Rs labeled "CRF", "Copy 1" and "Copy 2". The Sequence Listing of the CD-Rs is the same. The Sequence Listing, created on Mar. 8, 2006 and prepared in IBM-PC/MS-DOS format contains one 44.8 kb file, 6756.204 WO.ST25.txt.

FIELD OF THE INVENTION

The invention relates to novel peptides for use in therapy, in particular for the treatment of obesity and related diseases.

BACKGROUND OF THE INVENTION

Obesity is a well known risk factor for the development of many very common diseases such as atherosclerosis, hypertension, type 2 diabetes (non-insulin dependent diabetes mellitus (NIDDM)), dyslipidaemia, coronary heart disease, and osteoarthritis and various malignancies. It also causes considerable problems through reduced motility and decreased quality of life. The incidence of obesity and thereby also these diseases is increasing throughout the entire industrialised world. Only a few pharmacological treatments are available to date, namely Sibutramine (acting via serotonergic and noradrenaline mechanisms, Abbott) and Orlistat (reducing fat uptake from the gut, Roche Pharm). However, due to the important effect of obesity as a risk factor in serious and even mortal and common diseases there is still a need for pharmaceutical compounds useful in the treatment of obesity.

The term obesity implies an excess of adipose tissue. In this context obesity is best viewed as any degree of excess adiposity that imparts a health risk. The distinction between normal and obese individuals can only be approximated, but the health risk imparted by obesity is probably a continuum with increasing adiposity. However, in the context of the present invention, individuals with a body mass index (BMI=body weight in kilograms divided by the square of the height in meters) above 25 are to be regarded as obese.

Even mild obesity increases the risk for premature death, diabetes, hypertension, atherosclerosis, gallbladder disease and certain types of cancer. In the industrialized western world the prevalence of obesity has increased significantly in the past few decades. Because of the high prevalence of obesity and its health consequences, its treatment should be a high public health priority.

When energy intake exceeds energy expenditure, the excess calories are stored in adipose tissue, and if this net positive balance is prolonged, obesity results, i.e. there are two components to weight balance, and an abnormality on either side (intake or expenditure) can lead to obesity.

Pro-opiomelanocortin (POMC) is the precursor for β-endorphin and melanocortin peptides, including melanocyte stimulating hormone (α-MSH) and adrenocorticotropin (ACTH). POMC is expressed in several peripheral and central tissues including melanocytes, pituitary and neurones of the hypothalamus. The POMC precursor is processed differently in different tissues resulting in the expression of different melanocortin peptides depending on the site of expression. In the anterior lobe of the pituitary, mainly ACTH is produced whereas in the intermediate lobe and the hypothalamic neurones the major peptides are α-MSH, β-MSH, desacetyl-α-MSH and β-endorphin. Several of the melanocortin peptides, including ACTH and α-MSH, have been demonstrated to have appetite suppressing activity when injected intracerebroventricular in rats (Vergoni et al, European Journal of Pharmacology 179, 347-355 (1990)). An appetite suppressing effect is also obtained with the artificial cyclic α-MSH analogue, MT-II disclosed in U.S. Pat. No. 5,731,408.

A family of five melanocortin receptor subtypes has been identified (melanocortin receptor 1-5, also called MC1, MC2, MC3, MC4 and MC5). The MC1, MC2 and MC5 are mainly expressed in peripheral tissues whereas MC3 and MC4 are mainly centrally expressed, however MC3 are also expressed in several peripheral tissues. MC3 receptors have besides being involved in energy homeostasis also been suggested to be involved in several inflammatory diseases. An MC3 agonist could have a positive effect on these diseases, e.g. gouty arthritis. MC5 receptors are mainly peripheral expressed and has been suggested to be involved in exocrine secretion and in inflammation. The MC4 receptor is shown to be involved in the regulation of body weight and feeding behaviour as MC4 knock out mice develop obesity (Huzar et al, Cell 88, 131-141 (1997)). Furthermore studies of either ectopic centrally expression of agouti (MC1, MC3 and MC4 antagonist) or over-expression of an endogenously occurring MC3 and MC4 antagonist (agouti gene related peptide, AGRP) in the brain demonstrated that the over-expression of these two antagonists lead to the development of obesity (Kleibig et al, PNAS 92, 4728-4732 (1995)). Furthermore icv injection of a C-terminal fragment of AGRP increases feeding and antagonises the inhibitory effect of α-MSH on food intake.

In humans several cases of families with obesity presumably due to frame shift mutations in the MC4 receptor have been described (e.g. Yeo et al, Nature Genetics 20, 111-112 (1998), Vaisse et al, Nature Genetics 20, 113-114).

In conclusion, a MC4 agonist could serve as an anorectic drug, and be useful in the treatment of obesity or obesity related diseases as well as in the treatment of other diseases, disorders or conditions, which are improved by activation of the MC4 receptor.

MC4 antagonists may be useful for treatment of cachaxia, anorexia, and for treatment of waisting in frail elderly patients. Furthermore, MC4 antagonists may be used for treatment of chronic pain, neuropathy and neurogenic inflammation.

A large number of patent applications disclose small molecules as melanocortin receptor modulators, examples of which are WO 03/009850, WO 03/007949 and WO 02/081443.

The use of peptides as melanocortin receptor modulators is also disclosed in a number of patents. EP 292291 discloses a number of 7 amino acid residues derivatives of α-MSH with increased potency characterized, e.g. by a D-Phe at position 7 in the α-MSH sequence and by the presence of a disulfide bridge.

U.S. Pat. No. 5,731,408 discloses cyclic peptides, seven amino in length having D-2-Nal at position 4, which are MC-4 antagonists.

U.S. Pat. No. 4,457,864 discloses trideca-peptide analogues of α-MSH, which display increased potency and prolongation. Preferred compounds have Nle and D-Phe in position 4 and 7, respectively.

WO 98/27113 discloses peptides with specific binding affinity for melanocortin receptors comprising the structure X—Y-His-B-Arg-Z, wherein X and Y are amino acid residues, Z is an aromatic amino acid residue and B is D-(2-thienyl)alanine or D-(3-pyridyl)alanine.

An MT-II analogue with the structure Ac-Nle-c[Asp-Hyp-D-Phe-Arg-Trp-Lys]-$NH_2$ is disclosed in *Proc. $2^{nd}$ Inter. and $17^{th}$ American Peptide Symp.*, Jun. 9-14, 2001, San Diego, 992, 893; an MT-II analogue with the structure Ac-Nle-c[Asp-Ala-D-Phe-Arg-Trp-Lys]-$NH_2$ is disclosed in *Peptides*, 20(3), 1999, 401-409; an MT-II analogue with the structure Ac-Nle-c[Asp-Gln-D-Phe-Arg-Trp-Lys]-$NH_2$ is disclosed in *Bioorg. Med. Chem. Lett*, 13(7), 2003, 1307-1311; the two MT-II analogues Ac-Nle-c[Asp-Glu-D-Phe-Arg-Trp-Lys]-$NH_2$ and Ac-Nle-c[Asp-Lys-D-Phe-Arg-Trp-Lys]-$NH_2$ are disclosed in *Biochem. Res. Commun.*, 272(1), 2000, 23-28; and an MT-II analogue Ac-Nle-c[Asp-Pro-D-Phe-Arg-Trp-Lys]-$NH_2$ is mentioned in *J. Peptide Res.*, 62, 2003, 199-206.

It remains a challenge to provide melanocortin receptor modifiers which are highly potent and which have a suitable solubility and thus bioavailability in combination with an appropriate selectivity.

SUMMARY OF THE INVENTION

The present inventors have surprisingly found that specific MT-II analogues have a high modulating effect on one or more of the melanocortin receptors, i.e. MC1, MC2, MC3, MC4 and/or MC5 receptors. Accordingly, the invention relates to peptides of formula I

X1-X2-X3-X4-X5-X6-X7-$R^1$    (I)

wherein X1 represents Nle or X-Nle, wherein X represents an amino acid or a di-, tri-, tetra- or penta-peptide consisting of polar or hydrophilic amino acid residues selected from the D and L forms of Asp, Glu, His, Arg, homoArg, Tyr, Asn, Ser, Thr, Lys, Orn, Dap, Dab and Gln and wherein X may furthermore contain one or two amino acid residues selected from Gly, β-Ala or the D and L forms of Pro, Hyp, and Ala;

and wherein the N-terminal amino group of X1 may optionally be acylated with an acyl moiety, R—C(O)—, wherein R presents an alkyl or alkenyl with up to 6 carbon atoms, wherein said alkyl may optionally be substituted with one or more substituents selected from hydroxyl and amino;

X2 represents Glu, Asp, Cys, homoCys, Lys, Orn, Dab, Dap;

X3 represents Cit, Dab, Dap, cyclohexylglycine, cyclohexylalanine, Val, Ile, tert-butylglycine, Leu, Tyr, Glu, Ala, Nle, Met, Met(O), Met($O_2$), Gln, Gln(alkyl), Gln(aryl), Asn, Asn(alkyl), Asn(aryl), Ser, Thr, Cys, Pro, Hyp, Tic, 2-PyAla, 3-PyAla, 4-PyAla, (2-thienyl)alanine, 3-(thienyl)alanine, (4-thiazolyl)Ala, (2-furyl)alanine, (3-furyl)alanine, Phe, wherein the phenyl moiety of said Phe is optionally substituted by halogen, hydroxyl, alkoxy, nitro, benzoyl, methyl, trifluoromethyl, amino, or cyano;

X4 represents D-Phe, wherein the phenyl moiety in D-Phe may optionally be substituted with one or more substituents selected from amongst halogen, hydroxy, alkoxy, nitro, methyl, trifluoromethyl or cyano;

X5 represents Arg;

X6 represents Trp, 2-Nal, (3-benzo[b]thienyl)alanine or (S)-2,3,4,9-tetrahydro-1H-β-carboline-3-carboxylic acid;

X7 represents Glu, Asp, Cys, homoCys, Lys, Orn, Dab, Dap;

wherein there is a bond between X2 and X7 to make the peptide of formula I cyclic either by a disulfide bridge (X2 and X7 are both independently Cys or homoCys) or by a an amide bond formed from a carboxyl group in the side chain of X2 or X7 and an amino group in the side chain of X2 or X7;

$R^1$ represents —N(R")$_2$ or —OR" with each R" independently representing hydrogen or $C_{1-6}$alkyl, which may optionally be substituted with one or more amine or hydroxyl;

provided that if X3 represents Hyp, Ala, Pro, Glu, Lys or Gln, and X1 represents Ac—Nle, then X2 does not represent Asp;

and any pharmaceutically acceptable salt, solvate or prodrug thereof.

In another embodiment, the invention relates to the use of said peptide in therapy.

In another embodiment, the invention relates to therapeutic methods comprising the administration of said peptides to subjects in need thereof.

In still another embodiment, the invention relates to the use of said peptides in the manufacture of medicaments.

EXEMPLARY ASPECTS AND FEATURES OF THE INVENTION

To better illustrate the invention described herein, a non-limiting list of exemplary aspects and features of the invention is provided here:

1. A peptide according to formula I

X1-X2-X3-X4-X5-X6-X7-R1    (I)

wherein X1 represents Nle or X-Nle, wherein X represents an amino acid or a di-, tri-, tetra- or penta-peptide consisting of polar or hydrophilic amino acid residues selected from the D and L forms of Asp, Glu, His, Arg, homoArg, Tyr, Asn, Ser, Thr, Lys, Orn, Dap, Dab and Gln and wherein X may furthermore contain one or two amino acid residues selected from Gly, □-Ala or the D and L forms of Pro, Hyp, and Ala;

and wherein the N-terminal amino group of X1 may optionally be acylated with an acyl moi-ety, R—C(O)—, wherein R presents an alkyl or alkenyl with up to 6 carbon atoms, wherein said alkyl may optionally be substituted with one or more substituents selected from hydroxyl and amino;

X2 represents Glu, Asp, Cys, homoCys, Lys, Orn, Dab, Dap;

X3 represents Cit, Dab, Dap, cyclohexylglycine, cyclohexylalanine, Val, Ile, tert-butylglycine, Leu, Tyr, Glu, Ala, Nle, Met, Met(O), Met(O2), Gln, Gln(alkyl), Gln(aryl), Asn, Asn(alkyl), Asn(aryl), Ser, Thr, Cys, Pro, Hyp, Tic, 2-PyAla, 3-PyAla, 4-PyAla, (2-thienyl)alanine, 3-(thienyl)alanine, (4-thiazolyl)Ala, (2-furyl)alanine, (3-furyl)alanine, Phe, wherein the phenyl moiety of said Phe is optionally substituted by halogen, hydroxyl, alkoxy, nitro, benzoyl, methyl, trifluoromethyl, amino, or cyano;

X4 represents D-Phe, wherein the phenyl moiety in D-Phe may optionally be substituted with one or more substituents selected from amongst halogen, hydroxy, alkoxy, nitro, methyl, trifluoromethyl or cyano;

X5 represents Arg;

X6 represents Trp, 2-Nal, (3-benzo[b]thienyl)alanine or (S)-2,3,4,9-tetrahydro-1H-β-carboxylic acid;

X7 represents Glu, Asp, Cys, homoCys, Lys, Orn, Dab, Dap;

wherein there is a bond between X2 and X7 to make the peptide of formula I cyclic either by a disulfide bridge (X2 and X7 are both independently Cys or homocys) or by a an amide bond formed from a carboxyl group in the side chain of X2 or X7 and an amino group in the side chain of X2 or X7;

R1 represents —N(R")2 or —OR" with each R" independently representing hydrogen or C1-6alkyl, which may optionally be substituted with one or more amine or hydroxyl;

provided that if X3 represents Hyp, Ala, Pro, Glu, Lys or Gln, and X1 represents Ac-Nle, then X2 does not represent Asp;

and any pharmaceutically acceptable salt, solvate or prodrug thereof.

2. A compound according to aspect 1, wherein R1 represents —N(R")2, wherein each R" represents hydrogen, or wherein one R" represents C1-3alkyl optionally substituted with one or more substituents selected from hydroxyl and amino.

3. The compound according to aspect 1 or 2, wherein X1 represents Nle or R—C(O)-Nle.

4. The compound according to aspect 1 or 2, wherein X represents Z1-Z2-Z3-Z4-Z5, Z2-Z3-Z4-Z5, Z3-Z4-Z5, Z4-Z5 or Z5, wherein
Z1 represents an amino acid;
Z2 represents an amino acid;
Z3 represents Ser, Ala, Lys, Gln, Asn or D-Ser;
Z4 represents Tyr, Lys, His, Arg, homoArg, Gln or Asn; and
Z5 represents Ser, Dab, Ala, Hyp, Gly, Pro or Thr;
and wherein the N-terminus of X is acylated with R—C(O)—.

5. The compound according to aspect 4, wherein X represents
Ala-Lys-Tyr-Ser- (SEQ ID NO:1),
Ala-Lys-Ala-,
Asn-Arg-Gly-,
Asn-Arg-Hyp-,
Asn-Asn-Pro-,
Asn-Asn-Thr-,
Asn-His-Gly-,
Asn-His-Pro-,
Asn-homoArg-Hyp-,
Asn-homoArg-Thr-,
Asn-Tyr-Ser-,
Dab-,
D-Ser-Arg-Pro-,
D-Ser-Arg-Thr-,
D-Ser-Asn-Hyp-,
D-Ser-Asn-Ser-,
D-Ser-His-Ser-,
D-Ser-His-Thr-,
D-Ser-homoArg-Gly-,
D-Ser-homoArg-Pro-,
D-Ser-Tyr-Gly-,
D-Ser-Tyr-Hyp-,
Gln-Arg-Hyp-,
Gln-Arg-Ser-,
Gln-Asn-Pro-,
Gln-Asn-Thr-,
Gln-His-Hyp-,
Gln-His-Thr-,
Gln-homoArg-Gly-,
Gln-homoArg-Ser-,
Gln-Tyr-Gly-,
Gln-Tyr-Pro-,
Gly-Ser-Gln-His-Ser- (SEQ ID NO: 2),
Gly-Ser-Gln-homoArg-Ser- (SEQ ID NO: 3),
Ser-Arg-Gly-,
Ser-Arg-Pro-,
Ser-Arg-Ser-,
Ser-Arg-Thr-,
Ser-Asn-Gly-,
Ser-Asn-Ser-
Ser-Gln-His-Ser- (SEQ ID NO: 4),
Ser-Gln-Ser-,
Ser-His-Gly-,
Ser-His-Hyp-,
Ser-His-Pro-,
Ser-His-Ser-,
Ser-homoArg-Pro-,
Ser-homoArg-Ser-,
Ser-homoArg-Thr-,
Ser-,
Ser-Tyr-Hyp-,
Ser-Tyr-Ser- or
Ser-Tyr-Thr-, each of which is acylated at the N-terminus with R—C(O)—.

6. The compound according to any of aspects 1-5, wherein R represents alkyl with up to six carbon atoms, optionally substituted with one or more substituents selected from hydroxyl and amino.

7. The compound according to aspect 6, wherein R represents methyl, ethyl, propyl, butyl, pentyl and hexyl, optionally substituted with one or more substituents selected from hydroxyl and amino.

8. The compound according to aspect 6, wherein R represents 2-hydroxy-3-methylbutanoyl or 2,4-diaminobutanoyl.

9. The compound according to aspect 1-3, wherein X1 represents Ac-Nle.

10. The compound according to any of aspects 1-2 or 4-8, wherein X1 represents Ac-Gly-Ser-Gln-His-Ser-Nle (SEQ ID NO: 5) or Ac-Ser-His-Ser-Nle (SEQ ID NO: 6).

11. The compound according to any of aspects 1-10, wherein X3 represents Met(O2), Tic, 3-PyAla, Ser, Cit, Leu, Phe(4-amino), Phe(3,4-dichloro), Phe(3,4-difluoro), Dab, Cgl, Val, Cha, Phe, Dap, Ile, Thr, tBuGly, (4-thiazolyl)Ala, Hyp, Ans or Gln.

12. The compound according to any of aspects 1-11, wherein X3 represents Met(O2), Tic, 3-PyAla, Ser, Cit, Leu, Phe(4-amino), Phe(3,4-difluoro), Dab, Phe, Dap, Thr, (4-thiazolyl)Ala or Hyp.

13. The compound according to any of aspects 1-12, wherein X3 represents Tic, Met(O)2, Ser, Hyp, Cit, Dap, (4-thiazolyl)Ala or 3-PyAla.

14. The compound according to any of aspects 1-13, wherein X3 represents Met(O2), Hyp or 3-PyAla.

15. The compound according to any of aspects 1-14, wherein X4 represents D-Phe, D-Phe(4-chloro), D-Phe(4-iodo), D-Phe(3-trifluoromethyl), D-Phe(2-methyl) or D-Phe(2-chloro).

16. The compound according to any of aspects 1-15, wherein X4 represents D-Phe or D-Phe(4-chloro).

17. The compound according to any of aspects 1-16, wherein X4 represents D-Phe.

18. The compound according to any of aspects 1-17, wherein X6 represents Trp.

19. The compound according to any of aspects 1-18, wherein X2 represents Glu and X7 represents Lys.

20. The compound according to any of aspects 1-18, wherein X2 represents Asp and X7 represents Lys.

21. The compound according to any of aspects 1-13, wherein X2-X3-X4-X5-X6-X7 represents c[X2-X3-D-Phe-Trp-Lys], wherein X2 represents Glu or Asp; X3 represents Met(O2), Tic, 3-PyAla, Ser, Cit, Leu, Phe(4-amino), Phe (3,4-dichloro), Phe(3,4-difluoro), Dab, Cgl, Val, Cha, Phe, Dap, Ile, Thr, tBuGly, (4-thiazolyl)Ala or Hyp.

22. The compound according to aspect 21, wherein X2 represents Glu, and X3 represents Tic, Met(O)2, Ser, Hyp, Cit, Dap, (4-thiazolyl)Ala or 3-PyAla.

23. The compound according to aspect 22, wherein X3 represents Hyp

24. The compound according to aspect 21, wherein X2-X3-X4-X5-X6-X7 represents c[Glu-Hyp-D-Phe-Arg-Trp-Lys].

25. The compound according to aspect 1, wherein X3 represents Tic, Met(O)2, Ser, Hyp, Cit, Dap, (4-thiazolyl)Ala or 3-PyAla, and X1 represents Ac-Gly-Ser-Gln-His-Ser-Nle- (SEQ ID NO: 5) or Ac-Nle.

26. The compound according to aspect 1, wherein X3 represents Tic, Met(O)2, Ser, Hyp, Cit, Dap, (4-thiazolyl)Ala or 3-PyAla;
X1 represents Ac-Gly-Ser-Gln-His-Ser-Nle- (SEQ ID NO: 5) or Ac-Nle;
X4 represents D-Phe;
and X6 represents Trp;
and X2 represents Asp.

27. The compound according to aspect 1, wherein X3 represents Tic, Met(O)2, Ser, Hyp, Cit, Dap, (4-thiazolyl)Ala or 3-PyAla;
X1 represents Ac-Gly-Ser-Gln-His-Ser-Nle- (SEQ ID NO: 5) or Ac-Nle;
X4 represents D-Phe;
X6 represents Trp;
and X2 represents Glu.

28. The compound according to aspect 1 selected from
Ac-Nle-c[Glu-3-PyAla-D-Phe-Arg-Trp-Lys]-NH2 (SEQ ID NO: 6)
Ac-Nle-c[Glu-Leu-D-Phe-Arg-Trp-Lys]-NH2 (SEQ ID NO: 7)
Ac-Nle-c[Glu-Phe(3,4-dichloro)-D-Phe-Arg-Trp-Lys]-NH2 (SEQ ID NO: 8)
Ac-Nle-c[Glu-Met(O2)-D-Phe-Arg-Trp-Lys]-NH2 (SEQ ID NO: 9)
Ac-Nle-c[Glu-Dab-D-Phe-Arg-Trp-Lys]-NH2 (SEQ ID NO: 10)
Ac-Nle-c[Glu-Cgl-D-Phe-Arg-Trp-Lys]-NH2 (SEQ ID NO: 11)
Ac-Nle-c[Glu-Val-D-Phe-Arg-Trp-Lys]-NH2 (SEQ ID NO: 12)
Ac-Nle-c[Glu-Tic-D-Phe-Arg-Trp-Lys]-NH2 (SEQ ID NO: 13)
Ac-Nle-c[Glu-Cha-D-Phe-Arg-Trp-Lys]-NH2 (SEQ ID NO: 14)
Ac-Nle-c[Glu-Ile-D-Phe-Arg-Trp-Lys]-NH2 (SEQ ID NO: 15)
Ac-Nle-c[Glu-tBuGly-D-Phe-Arg-Trp-Lys]-NH2 (SEQ ID NO: 16)
Ac-Nle-c[Glu-Phe(3,4-difluoro)-D-Phe-Arg-Trp-Lys]-NH2 (SEQ ID NO: 17)
Ac-Nle-c[Glu-Phe-D-Phe-Arg-Trp-Lys]-NH2 (SEQ ID NO: 18)
Ac-Ser-Tyr-Ser-Nle-c[Glu-3-PyAla-D-Phe-Arg-Trp-Lys]-NH2 (SEQ ID NO: 19)
H-Ala-Lys-Tyr-Ser-Nle-c[Glu-3-PyAla-D-Phe-Arg-Trp-Lys]-NH2 (SEQ ID NO: 20)
2-Hydroxy-3-methylbutanoyl-Ser-Nle-c[Glu-3-PyAla-D-Phe-Arg-Trp-Lys]-NH2 (SEQ ID NO: 21)
H-Dab-Nle-c[Glu-3-PyAla-D-Phe-Arg-Trp-Lys]-NH2 (SEQ ID NO: 22)
H-Ala-Lys-Ala-Nle-c[Glu-Hyp-D-Phe-Arg-Trp-Lys]-NH2 (SEQ ID NO: 23)
Ac-Nle-c[Glu-Hyp-D-Phe(4-iodo)-Arg-Trp-Lys]-NH2 (SEQ ID NO: 24)
Hex-5-enoyl-Nle-c[Glu-Hyp-D-Phe-Arg-Trp-Lys]-NH2 (SEQ ID NO: 25)
Ac-Gly-Ser-Gln-His-Ser-Nle-c[Glu-Hyp-D-Phe-Arg-Trp-Lys]-NH2 (SEQ ID NO: 26)
Ac-Gly-Ser-Gln-homoArg-Ser-Nle-c[Glu-Hyp-D-Phe-Arg-Trp-Lys]-NH2 (SEQ ID NO: 27)
Ac-Gly-Ser-Gln-His-Ser-Nle-c[Glu-Met(O2)-D-Phe-Arg-Trp-Lys]-NH2 (SEQ ID NO: 28)
Ac-Nle-c[Glu-Hyp-D-Phe-Arg-Trp-Lys]-NH2 (SEQ ID NO: 29)
Ac-Nle-c[Glu-Hyp-D-Phe-Arg-Trp-Lys]-(2-aminoethyl)amide (SEQ ID NO: 30)
Ac-Nle-c[Asp-Phe(4-amino)-D-Phe(4-chloro)-Arg-Trp-Lys]-NH2 (SEQ ID NO: 31)
Ac-Asn-Tyr-Ser-Nle-c[Glu-Hyp-D-Phe-Arg-Trp-Lys]-NH2 (SEQ ID NO: 32)
Ac-D-Ser-His-Ser-Nle-c[Glu-Hyp-D-Phe-Arg-Trp-Lys]-NH2 (SEQ ID NO: 33)
Ac-Gln-Arg-Ser-Nle-c[Glu-Hyp-D-Phe-Arg-Trp-Lys]-NH2 (SEQ ID NO: 34)
Ac-Ser-homoArg-Ser-Nle-c[Glu-Hyp-D-Phe-Arg-Trp-Lys]-NH2 (SEQ ID NO: 35)
Ac-Gln-homoArg-Ser-Nle-c[Glu-Hyp-D-Phe-Arg-Trp-Lys]-NH2 (SEQ ID NO: 36)
Ac-Ser-Asn-Ser-Nle-c[Glu-Hyp-D-Phe-Arg-Trp-Lys]-NH2 (SEQ ID NO: 37)
Ac-D-Ser-Asn-Ser-Nle-c[Glu-Hyp-D-Phe-Arg-Trp-Lys]-NH2 (SEQ ID NO: 38)
Ac-Ser-Tyr-Hyp-Nle-c[Glu-Hyp-D-Phe-Arg-Trp-Lys]-NH2 (SEQ ID NO: 39)
Ac-D-Ser-Tyr-Hyp-Nle-c[Glu-Hyp-D-Phe-Arg-Trp-Lys]-NH2 (SEQ ID NO: 40)
Ac-Ser-His-Hyp-Nle-c[Glu-Hyp-D-Phe-Arg-Trp-Lys]-NH2 (SEQ ID NO: 41)
Ac-Gln-His-Hyp-Nle-c[Glu-Hyp-D-Phe-Arg-Trp-Lys]-NH2 (SEQ ID NO: 42)
Ac-Gln-Arg-Hyp-Nle-c[Glu-Hyp-D-Phe-Arg-Trp-Lys]-NH2 (SEQ ID NO: 43)
Ac-Asn-Arg-Hyp-Nle-c[Glu-Hyp-D-Phe-Arg-Trp-Lys]-NH2 (SEQ ID NO: 44)
Ac-Asn-homoArg-Hyp-Nle-c[Glu-Hyp-D-Phe-Arg-Trp-Lys]-NH2 (SEQ ID NO: 45)
Ac-D-Ser-Asn-Hyp-Nle-c[Glu-Hyp-D-Phe-Arg-Trp-Lys]-NH2 (SEQ ID NO: 46)
Ac-Gln-Tyr-Pro-Nle-c[Glu-Hyp-D-Phe-Arg-Trp-Lys]-NH2 (SEQ ID NO: 47)
Ac-Ser-His-Pro-Nle-c[Glu-Hyp-D-Phe-Arg-Trp-Lys]-NH2 (SEQ ID NO: 48)
Ac-Asn-His-Pro-Nle-c[Glu-Hyp-D-Phe-Arg-Trp-Lys]-NH2 (SEQ ID NO: 49)
Ac-Ser-Arg-Pro-Nle-c[Glu-Hyp-D-Phe-Arg-Trp-Lys]-NH2 (SEQ ID NO: 50)
Ac-D-Ser-Arg-Pro-Nle-c[Glu-Hyp-D-Phe-Arg-Trp-Lys]-NH2 (SEQ ID NO: 51)
Ac-Ser-homoArg-Pro-Nle-c[Glu-Hyp-D-Phe-Arg-Trp-Lys]-NH2 (SEQ ID NO: 52)
Ac-D-Ser-homoArg-Pro-Nle-c[Glu-Hyp-D-Phe-Arg-Trp-Lys]-NH2 (SEQ ID NO: 53)
Ac-Gln-Asn-Pro-Nle-c[Glu-Hyp-D-Phe-Arg-Trp-Lys]-NH2 (SEQ ID NO: 54)
Ac-Asn-Asn-Pro-Nle-c[Glu-Hyp-D-Phe-Arg-Trp-Lys]-NH2 (SEQ ID NO: 55)
Ac-Ser-Tyr-Thr-Nle-c[Glu-Hyp-D-Phe-Arg-Trp-Lys]-NH2 (SEQ ID NO: 56)

Ac-D-Ser-His-Thr-Nle-c[Glu-Hyp-D-Phe-Arg-Trp-Lys]-NH2 (SEQ ID NO: 57)
Ac-Gln-His-Thr-Nle-c[Glu-Hyp-D-Phe-Arg-Trp-Lys]-NH2 (SEQ ID NO: 58)
Ac-Ser-Arg-Thr-Nle-c[Glu-Hyp-D-Phe-Arg-Trp-Lys]-NH2 (SEQ ID NO: 59)
Ac-D-Ser-Arg-Thr-Nle-c[Glu-Hyp-D-Phe-Arg-Trp-Lys]-NH2 (SEQ ID NO: 60)
Ac-Ser-homoArg-Thr-Nle-c[Glu-Hyp-D-Phe-Arg-Trp-Lys]-NH2 (SEQ ID NO: 61)
Ac-Asn-homoArg-Thr-Nle-c[Glu-Hyp-D-Phe-Arg-Trp-Lys]-NH2 (SEQ ID NO: 62)
Ac-Gln-Asn-Thr-Nle-c[Glu-Hyp-D-Phe-Arg-Trp-Lys]-NH2 (SEQ ID NO: 63)
Ac-Asn-Asn-Thr-Nle-c[Glu-Hyp-D-Phe-Arg-Trp-Lys]-NH2 (SEQ ID NO: 64)
Ac-D-Ser-Tyr-Gly-Nle-c[Glu-Hyp-D-Phe-Arg-Trp-Lys]-NH2 (SEQ ID NO: 65)
Ac-Gln-Tyr-Gly-Nle-c[Glu-Hyp-D-Phe-Arg-Trp-Lys]-NH2 (SEQ ID NO: 66)
Ac-Ser-His-Gly-Nle-c[Glu-Hyp-D-Phe-Arg-Trp-Lys]-NH2 (SEQ ID NO: 67)
Ac-Asn-His-Gly-Nle-c[Glu-Hyp-D-Phe-Arg-Trp-Lys]-NH2 (SEQ ID NO: 68)
Ac-Ser-Arg-Gly-Nle-c[Glu-Hyp-D-Phe-Arg-Trp-Lys]-NH2 (SEQ ID NO: 69)
Ac-Asn-Arg-Gly-Nle-c[Glu-Hyp-D-Phe-Arg-Trp-Lys]-NH2 (SEQ ID NO: 70)
Ac-D-Ser-homoArg-Gly-Nle-c[Glu-Hyp-D-Phe-Arg-Trp-Lys]-NH2 (SEQ ID NO: 71)
Ac-Gln-homoArg-Gly-Nle-c[Glu-Hyp-D-Phe-Arg-Trp-Lys]-NH2 (SEQ ID NO: 72)
Ac-Ser-Asn-Gly-Nle-c[Glu-Hyp-D-Phe-Arg-Trp-Lys]-NH2 (SEQ ID NO: 73)
Ac-Ser-Tyr-Ser-Nle-c[Glu-Hyp-D-Phe-Arg-Trp-Lys]-NH2 (SEQ ID NO: 74)
Ac-Ser-His-Ser-Nle-c[Glu-Hyp-D-Phe-Arg-Trp-Lys]-NH2 (SEQ ID NO: 75)
Ac-Ser-Arg-Ser-Nle-c[Glu-Hyp-D-Phe-Arg-Trp-Lys]-NH2 (SEQ ID NO: 76)
Ac-Ser-His-Ser-Nle-c[Asp-Hyp-D-Phe-Arg-Trp-Lys]-NH2 (SEQ ID NO: 77)
Ac-Ser-His-Ser-Nle-c[Glu-Ser-D-Phe-Arg-Trp-Lys]-NH2 (SEQ ID NO: 78)
Ac-Ser-His-Ser-Nle-c[Glu-Hyp-D-Phe(3-trifluoromethyl)-Arg-Trp-Lys]-NH2 (SEQ ID NO: 79)
Ac-Ser-His-Ser-Nle-c[Glu-Hyp-D-Phe(2-methyl)-Arg-Trp-Lys]-NH2 (SEQ ID NO: 80)
Ac-Ser-His-Ser-Nle-c[Glu-Hyp-D-Phe(2-chloro)-Arg-Trp-Lys]-NH2 (SEQ ID NO: 81)
Ac-Nle-c[Asp-Thr-D-Phe-Arg-Trp-Lys]-NH2 (SEQ ID NO: 82)
Ac-Nle-c[Asp-Dap-D-Phe-Arg-Trp-Lys]-NH2 (SEQ ID NO: 83)
Ac-Nle-c[Asp-(4-thiazolyl)Ala-D-Phe-Arg-Trp-Lys]-NH2 (SEQ ID NO: 84)
Ac-Nle-c[Asp-Phe(4-amino)-D-Phe-Arg-Trp-Lys]-NH2 (SEQ ID NO: 85)
Ac-Nle-c[Asp-Cit-D-Phe-Arg-Trp-Lys]-NH2 (SEQ ID NO: 86) and
Ac-Ser-His-Ser-Nle-c[Asp-(4-thiazolyl)Ala-D-Phe-Arg-Trp-Lys]-NH2 (SEQ ID NO: 87).

29. A method of delaying the progression from IGT to type 2 diabetes, the method comprising administering to a patient in need thereof an effective amount of a compound of accord-ing to any of aspects 1-28, optionally in combination with one or more additional therapeutically active compound.

30. A method of delaying the progression from type 2 diabetes to insulin requiring diabetes, the method comprising administering to a patient in need thereof an effective amount of a compound according to any of aspects 1-28, optionally in combination with one or more additional therapeutically active compound.

31. A method of treating obesity or preventing overweight, the method comprising administering to a patient in need thereof an effective amount of a compound of according to any of aspects 1-28, optionally in combination with one or more additional therapeutically active com-pound.

32. A method of regulating the appetite, the method compris-ing administering to a patient in need thereof an effective amount of a compound of according to any of aspects 1-28, option-ally in combination with one or more additional therapeutically active compound.

33. A method of inducing satiety, the method comprising administering to a patient in need thereof an effective amount of a compound of according to any of aspects 1-28, optionally in combination with one or more additional therapeutically active compound.

34. A method of preventing weight gain after successfully having lost weight, the method comprising administering to a patient in need thereof an effective amount of a com-pound ac-cording to any of aspects 1-28, optionally in combination with one or more additional therapeutically active compound.

35. A method of increasing energy expenditure, the method comprising administering to a patient in need thereof an effective amount of a compound according to any of aspects 1-28, optionally in combination with one or more additional therapeutically active compound.

36. A method of treating a disease or state related to over-weight or obesity, the method comprising administering to a patient in need thereof an effective amount of a com-pound of according to any of aspects 1-28, optionally in combination with one or more additional therapeutically active compound.

37. A method of treating bulimia, the method comprising administering to a patient in need thereof an effective amount of a compound of according to any of aspects 1-28, optionally in combination with one or more additional therapeutically active compound.

38. A method of treating a disease or state selected from atherosclerosis, hypertension, diabetes, type 2 diabetes, impaired glucose tolerance (IGT), dyspilidemia, coronary heart disease, gallbladder disease, gall stone, osteoarthritis, cancer, sexual dysfunction and the risk of premature death, the method comprising administering to a patient in need thereof an effective amount of a compound of according to any of aspects 1-28, optionally in combination with one or more additional therapeutically active compound.

39. A method of treating in obese patients diseases or states selected from amongst type 2 diabetes, impaired glucose tolerance (IGT), dyspilidemia, coronary heart disease, gallbladder disease, gall stone, osteoarthritis, cancer, sexual dysfunction and the risk of premature death in obese patients, the method comprising administering to a patient in need thereof an effective amount of a compound of according to any of aspects 1-28, optionally in combination with one or more additional therapeutically active com-pound.

40. The method according to any of aspects 29-39, wherein said additional therapeutically active compound is selected from amongst antidiabetic agents, antihyperlipidemic agents, antiobesity agents, antihypertensive agents and agents for the treatment of complications resulting from or associated with diabetes.

41. The method according to any of aspects 29-39, wherein the compound according to any of aspects 1-28 is administered to a patient in a unit dosage form comprising about 0.05 mg to about 1000 mg.

42. The method according to any of aspects 29-41, wherein the compound according to any of aspects 1-28 is administered parenterally or sublingually.

43. The method according to aspect 42, wherein the compound according to any of aspects 1-28 is administered parenterally in a continuous or interrupted continuous dosing regime.

44. The method according to aspect 43, wherein a pump is used, said pump being either external or implanted into the patient to be treated.

45. A compound according to any of aspects 1-28 for use in therapy.

46. A pharmaceutical composition comprising a compound according to any of aspects 1-28, optionally in combination with another therapeutically active ingredient selected from amongst antidiabetic agents, antihyperlipidemic agents, antiobesity agents, antihypertensive agents and agents for the treatment of complications resulting from or associated with diabe-tes.

47. The composition according to aspect 46, comprising 0.1-2000 mg of a compound ac-cording to any of aspects 1-28 in a unit dosage form.

48. The use of a compound according to any of aspects 1-28 in the manufacture of a medica-ment for delaying the progression from IGT to type 2 diabetes, delaying the progression from type 2 diabetes to insulin requiring diabetes, treating obesity or preventing overweight, regu-lating the appetite, inducing satiety, preventing weight regain after successful weight loss, increasing energy expenditure, treating a disease or state related to overweight or obesity, treating bulimia, treating atherosclerosis, hypertension, type 2 diabetes, impaired glucose tolerance (IGT), dyspili-demia, coronary heart disease, gallbladder disease, gall stone, os-teoarthritis, cancer, sexual dysfunction and the risk of premature death, or for treating in obese patients diseases or states selected from amongst type 2 diabetes, impaired glucose tolerance (IGT), dyspilidemia, coronary heart disease, gallbladder disease, gall stone, os-teoarthritis, cancer, sexual dysfunction and the risk of premature death.

49. The use according to aspect 48, wherein said medicament is intended for obese patients.

These aspects are more fully described in, and additional aspects, features, and advantages of the invention will be apparent from, the description of the invention provided herein.

DEFINITIONS

The term "alkyl" as used herein without prefixes refers to a straight or branched chain saturated monovalent hydrocarbon radical having for instance from one to ten carbon atoms, for example $C_{1-8}$-alkyl. Typical $C_{1-8}$-alkyl groups include, e.g. methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-pentyl, n-hexyl, 1,2-dimethylpropyl, 2,2-dimethylpropyl, 1,2,2-trimethylpropyl and the like. The term "$C_{1-8}$-alkyl" as used herein also includes secondary $C_{3-8}$-alkyl and tertiary $C_{4-8}$-alkyl. More generally, the term "alkyl" is intended to indicate both primary, secondary and tertiary alkyl.

The term "alkenyl" as used herein without prefixes refers to a straight or branched chain monovalent hydrocarbon radical comprising at least one carbon-carbon double bond and having for instance from two to ten carbon atoms, for example $C_{2-8}$-alkyl. Typical $C_{2-8}$-alkenyl groups include, e.g. vinyl, allyl, 1-propenyl, 1,3-butadiene-1-yl and hex-5-enyl.

The term "halogen" is intended to indicate fluoro, chloro, bromo and iodo.

The term "alkoxy" is intended to indicate a radical of the formula —O—R', wherein R' is alkyl as indicated above.

In the present context, the term "aryl" is intended to indicate a carbocyclic aromatic ring radical or a fused aromatic ring system radical wherein at least one of the rings are aromatic. Typical aryl groups include phenyl, biphenylyl, naphthyl, and the like.

The amino acid abbreviations used in the present context have the following meanings

| | |
|---|---|
| Ac | $H_3C—C(O)—$ |
| Ala | alanine |
| Asn | asparagine |
| Asn(alkyl) | 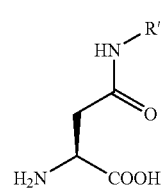 R' = alkyl |
| Asn(aryl) | 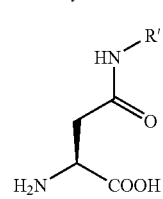 R' = aryl |
| Asp | aspartic acid |
| Arg | arginine |
| β-Ala | 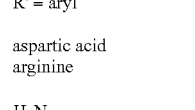 |
| Cha | 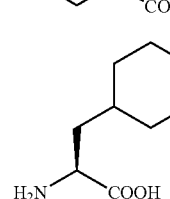 cyclohexylalanine |
| Cgl | 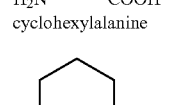 cyclohexylglycine |
| Cit | citrulline |
| Cys | cysteine |
| Dab | (S)-2,4-diaminobutyric acid |

-continued

| | | |
|---|---|---|
| Dap | (S)-2,3-diaminopropionic acid | |
| D-Phe | 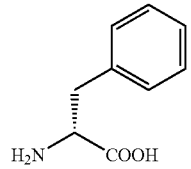 | |
| Gln | Glutamine | |
| Gln(alkyl) | 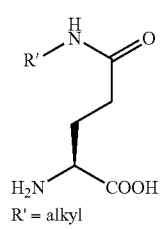 R' = alkyl | |
| Gln(aryl) | 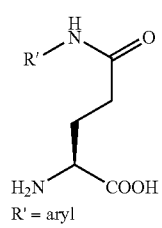 R' = aryl | |
| Glu | glutamic acid | |
| His | histidine | |
| homoArg | 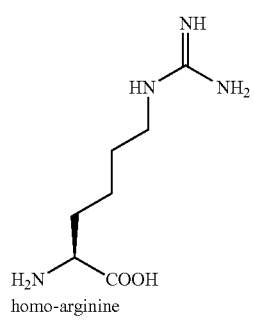 homo-arginine | |
| homoCys | 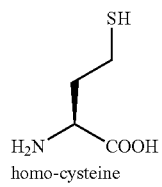 homo-cysteine | |
| Hyp | 4-hydroxyproline | |
| Ile | isoleucine | |
| Leu | leucine | |
| Lys | lysine | |
| Met | methionine | |
| Met(O) | 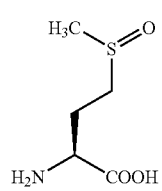 | |

-continued

| | | |
|---|---|---|
| Met($O_2$) | 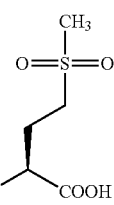 | |
| 1-Nal | 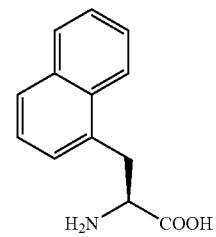 | |
| 2-Nal | 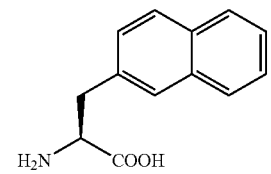 | |
| Nle | 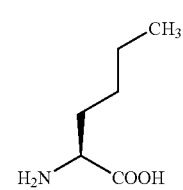 norleucine | |
| Orn | ornithine | |
| Phe | phenylalanine | |
| Pro | proline | |
| 2-PyAla | 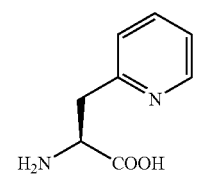 | |
| 3-PyAla | 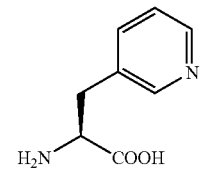 | |
| 4-PyAla | 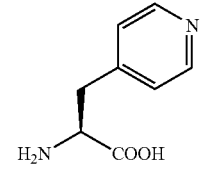 | |
| Ser | serine | |

-continued

| | |
|---|---|
| tBuGly | 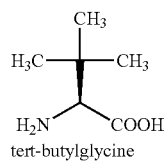
tert-butylglycine |
| Thr | threonine |
| (4-thiazolyl)Ala | 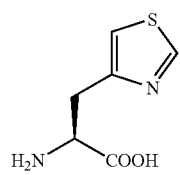 |
| Tic | 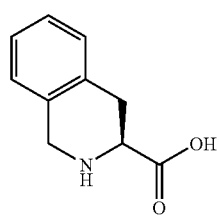 |
| Tyr | tyrosine |
| Trp | tryptophane |
| Val | valine |

In the present context, the term "agonist" is intended to indicate a substance that activates the receptors.

In the present context, the term "antagonist" is intended to indicate a substance that neutralizes or counteracts the effect of an agonist by binding to the corresponding receptor.

In the present context, the term "pharmaceutically acceptable salt" is intended to indicate salts which are not harmful to the patient. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

A "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The patient to be treated is preferably a mammal, in particular a human being, but it may also include animals, such as dogs, cats, cows, sheep and pigs.

As used herein, the term "solvate" is a complex of defined stoichiometry formed by a solute (in casu, a compound according to the present invention) and a solvent. Solvents may be, by way of example, water, ethanol, or acetic acid.

DESCRIPTION OF THE INVENTION

In one embodiment, X1 represents Nle or R—C(O)-Nle, wherein R represent an alkyl or alkenyl comprising up to 6 carbon atoms.

In one embodiment, R represents alkyl with up to six carbon atoms, such as methyl, ethyl, propyl, butyl, pentyl and hexyl. Particular mentioning is made of methyl. Said alkyl may be substituted with one or more substituents selected from hydroxyl and amino.

In one embodiment, $R^1$ represents —N(R")$_2$, wherein each R" represents hydrogen, or wherein one R" represents $C_{1-3}$alkyl, such as methyl, ethyl or propyl, which may optionally be substituted with amino, such as 2-amino-ethyl.

In one embodiment, X represents Z1-Z2-Z3-Z4-Z5, Z2-Z3-Z4-Z5, Z3-Z4-Z5, Z4-Z5 or Z5, wherein
Z1 represents an amino acid, and in particular Gly;
Z2 represents an amino acid, and in particular Ser or Ala;
Z3 represents Ser, Ala, Lys, Gln, Asn or D-Ser;
Z4 represents Tyr, Lys, His, Arg, homoArg, Gln or Asn; and
Z5 represents Ser, Dab, Ala, Hyp, Gly, Pro or Thr;
and wherein the N-terminus of X is acylated with R—C(O)—, wherein R represents an alkyl comprising up to 6 carbon atoms, such as methyl, ethyl, propyl, butyl, pentyl and hexyl, and in particular methyl. Said alkyl may also be substituted with one or more substituents selected from hydroxyl and amino. Particular mentioning is made of 2-hydroxy-3-methylbutanoyl and 2,4-diaminobutanoyl.

In one embodiment, X represents
Ala-Lys-Tyr-Ser- (SEQ ID NO: 1),
Ala-Lys-Ala-,
Asn-Arg-Gly-,
Asn-Arg- Hyp-,
Asn-Asn- Pro-,
Asn-Asn-Thr-,
Asn-His-Gly-,
Asn-His-Pro-, Asn-homoArg-Hyp-,
Asn-homoArg-Thr-,
Asn-Tyr-Ser-,
Dab-,
D-Ser-Arg- Pro-,
D-Ser-Arg-Thr-,
D-Ser-Asn-Hyp-,
D-Ser-Asn-Ser-,
D-Ser-His-Ser-,
D-Ser-His-Thr-,
D-Ser-homoArg-Gly-,
D-Ser-homoArg-Pro-,
D-Ser-Tyr-Gly-,
D-Ser-Tyr- Hyp-,
Gln-Arg-Hyp-,
Gln-Arg-Ser-,
Gln-Asn-Pro-,
Gln-Asn-Thr-,
Gln-His-Hyp-,
Gln-His-Thr-,
Gln-homoArg-Gly-,
Gln-homoArg-Ser-,
Gln-Tyr-Gly-,
Gln-Tyr-Pro-,
Gly-Ser-Gln-His-Ser- (SEQ ID NO: 2),
Gly-Ser-Gln-homoArg-Ser- (SEQ ID NO: 3),
Ser-Arg-Gly-,
Ser-Arg-Pro-,
Ser-Arg-Ser-,
Ser-Arg-Thr-,
Ser-Asn-Gly-,
Ser-Asn-Ser-
Ser-Gln-His-Ser- (SEQ ID NO: 4),
Ser-Gln-Ser-,
Ser-His-Gly-,
Ser-His-Hyp-,
Ser-His-Pro-,
Ser-His-Ser-,
Ser-homoArg-Pro-,
Ser-homoArg-Ser-,
Ser-homoArg-Thr-,
Ser-,
Ser-Tyr- Hyp-,
Ser-Tyr-Ser- or
Ser-Tyr-Thr-, each of which is acylated at the N-terminus with R—C(O)—, wherein R represents an alkyl comprising up to 6 carbon atoms, such as methyl, ethyl, propyl, butyl, pentyl and hexyl, and in particular methyl. Said alkyl may also be substituted with one or more substituents selected from hydroxyl and amino. Particular mentioning is made of 2-hydroxy-3-methylbutanoyl and 2,4-diaminobutanoyl.

In one embodiment, X1 represents Ac-Nle.

In on embodiment, X1 represents Ac-Gly-Ser-Gln-His-Ser-Nle (SEQ ID NO: 5).

in one embodiment, X1 represents Ac-Ser-His-Ser-Nle (SEQ ID NO: 88).

In one embodiment, X3 represents Met(O$_2$), Tic, 3-PyAla, Ser, Cit, Leu, Phe(4-amino), Phe(3,4-dichloro), Phe(3,4-difluoro), Dab, Cgl, Val, Cha, Phe, Dap, Ile, Thr, tBuGly, (4-thiazolyl)Ala or Hyp.

In one embodiment, X3 represents Met(O$_2$), Tic, 3-PyAla, Ser, Cit, Leu, Phe(4-amino), Phe(3,4-difluoro), Dab, Phe, Dap, Thr, (4-thiazolyl)Ala, Hyp, Ans or Gln.

In one embodiment, X3 represents Tic, Met(O)$_2$, Ser, Hyp, Cit, Dap, (4-thiazolyl)Ala or 3-PyAla.

In one embodiment, X3 represents Met(O2).

In one embodiment, X3 represents Hyp or 3-PyAla.

In one embodiment, X4 represents D-Phe, D-Phe(4-chloro), D-Phe(4-iodo), D-Phe(3-trifluoromethyl), D-Phe(2-methyl) or D-Phe(2-chloro).

In one embodiment, X4 represents D-Phe or D-Phe(4-chloro), and in particular D-Phe.

In one embodiment, X6 represents Trp.

In one embodiment, X2 represents Glu and X7 represents Lys, and in another embodiment, X2 represents Asp and X7 represents Lys.

In one embodiment, X2-X3-X4-X5-X6-X7 represents c[X2-X3-D-Phe-Arg-Trp-Lys], wherein X2 represents Glu or Asp and X3 represents Met(O$_2$), Tic, 3-PyAla, Ser, Cit, Leu, Phe(4-amino), Phe(3,4-dichloro), Phe(3,4-difluoro), Dab, Cgl, Val, Cha, Phe, Dap, Ile, Thr, tBuGly, (4-thiazolyl)Ala or Hyp. In particular, X2 may represent Glu. In particular, X3 may represent Tic, Met(O)$_2$, Ser, Hyp, Cit, Dap, (4-thiazolyl)Ala or 3-PyAla, and special mentioning is made of Hyp.

In one embodiment, X2-X3-X4-X5-X6-X7 represents c[Glu-Hyp-D-Phe-Arg-Trp-Lys].

In one embodiment, X3 represents Tic, Met(O)$_2$, Ser, Hyp, Cit, Dap, (4-thiazolyl)Ala or 3-PyAla, and X1 represents Ac-Gly-Ser-Gln-His-Ser-Nle- (SEQ ID NO: 5) or Ac-Nle.

In one embodiment, X3 represents Tic, Met(O)$_2$, Ser, Hyp, Cit, Dap, (4-thiazolyl)Ala or 3-PyAla, X1 represents Ac-Gly-Ser-Gln-His-Ser-Nle- (SEQ ID NO: 5) or Ac-Nle, and X4 represents D-Phe and X6 represents Trp, and X2 represents Asp.

In one embodiment, X3 represents Tic, Met(O)$_2$, Ser, Hyp, Cit, Dap, (4-thiazolyl)Ala or 3-PyAla, X1 represents Ac-Gly-Ser-Gln-His-Ser-Nle- (SEQ ID NO: 5) or Ac-Nle, and X4 represents D-Phe, and X6 represents Trp, and X2 represents Glu.

In one embodiment, the peptides of the present invention is selected from amongst Ac-Nle-c[Glu-3-PyAla-D-Phe-Arg-Trp-Lys]-NH$_2$ (SEQ ID NO: 6)
Ac-Nle-c[Glu-Leu-D-Phe-Arg-Trp-Lys]-NH$_2$ (SEQ ID NO: 7)
Ac-Nle-c[Glu-Phe(3,4-dichloro)-D-Phe-Arg-Trp-Lys]-NH$_2$ (SEQ ID NO: 8)
Ac-Nle-c[Glu-Met(O$_2$)-D-Phe-Arg-Trp-Lys]-NH$_2$ (SEQ ID NO: 9)
Ac-Nle-c[Glu-Dab-D-Phe-Arg-Trp-Lys]-NH$_2$ (SEQ ID NO: 10)
Ac-Nle-c[Glu-Cgl-D-Phe-Arg-Trp-Lys]-NH$_2$ (SEQ ID NO: 11)
Ac-Nle-c[Glu-Val-D-Phe-Arg-Trp-Lys]-NH$_2$ (SEQ ID NO: 12)
Ac-Nle-c[Glu-Tic-D-Phe-Arg-Trp-Lys]-NH$_2$ (SEQ ID NO: 13)
Ac-Nle-c[Glu-Cha-D-Phe-Arg-Trp-Lys]-NH$_2$ (SEQ ID NO: 14)
Ac-Nle-c[Glu-Ile-D-Phe-Arg-Trp-Lys]-NH$_2$ (SEQ ID NO: 15)
Ac-Nle-c[Glu-tBuGly-D-Phe-Arg-Trp-Lys]-NH$_2$ (SEQ ID NO: 16)
Ac-Nle-c[Glu-Phe(3,4-difluoro)-D-Phe-Arg-Trp-Lys]-NH$_2$ (SEQ ID NO: 17)
Ac-Nle-c[Glu-Phe-D-Phe-Arg-Trp-Lys]-NH$_2$ (SEQ ID NO: 18)
Ac-Ser-Tyr-Ser-Nle-c[Glu-3-PyAla-D-Phe-Arg-Trp-Lys]-NH$_2$ (SEQ ID NO: 19)
H-Ala-Lys-Tyr-Ser-Nle-c[Glu-3-PyAla-D-Phe-Arg-Trp-Lys]-NH$_2$ (SEQ ID NO: 20)
2-Hydroxy-3-methylbutanoyl-Ser-Nle-c[Glu-3-PyAla-D-Phe-Arg-Trp-Lys]-NH$_2$ (SEQ ID NO: 21)

H-Dab-Nle-c[Glu-3-PyAla-D-Phe-Arg-Trp-Lys]-NH₂ (SEQ ID NO: 22)
H-Ala-Lys-Ala-Nle-c[Glu-Hyp-D-Phe-Arg-Trp-Lys]-NH₂ (SEQ ID NO: 23)
Ac-Nle-c[Glu-Hyp-D-Phe(4-iodo)-Arg-Trp-Lys]-NH₂ (SEQ ID NO: 24)
Hex-5-enoyl-Nle-c[Glu-Hyp-D-Phe-Arg-Trp-Lys]-NH₂ (SEQ ID NO: 25)
Ac-Gly-Ser-Gln-His-Ser-Nle-c[Glu-Hyp-D-Phe-Arg-Trp-Lys]-NH₂ (SEQ ID NO: 26)
Ac-Gly-Ser-Gln-homoArg-Ser-Nle-c[Glu-Hyp-D-Phe-Arg-Trp-Lys]-NH₂ (SEQ ID NO: 27)
Ac-Gly-Ser-Gln-His-Ser-Nle-c[Glu-Met(O2)-D-Phe-Arg-Trp-Lys]-NH₂ (SEQ ID NO: 28)
Ac-Nle-c[Glu-Hyp-D-Phe-Arg-Trp-Lys]-NH₂ (SEQ ID NO: 29)
Ac-Nle-c[Glu-Hyp-D-Phe-Arg-Trp-Lys]-(2-aminoethyl) amide (SEQ ID NO: 30)
Ac-Nle-c[Asp-Phe(4-amino)-D-Phe(4-chloro)-Arg-Trp-Lys]-NH₂ (SEQ ID NO: 31)
Ac-Asn-Tyr-Ser-Nle-c[Glu-Hyp-D-Phe-Arg-Trp-Lys]-NH₂ (SEQ ID NO: 32)
Ac-D-Ser-His-Ser-Nle-c[Glu-Hyp-D-Phe-Arg-Trp-Lys]-NH₂ (SEQ ID NO: 33)
Ac-Gln-Arg-Ser-Nle-c[Glu-Hyp-D-Phe-Arg-Trp-Lys]-NH₂ (SEQ ID NO: 34)
Ac-Ser-homoArg-Ser-Nle-c[Glu-Hyp-D-Phe-Arg-Trp-Lys]-NH₂ (SEQ ID NO: 35)
Ac-Gln-homoArg-Ser-Nle-c[Glu-Hyp-D-Phe-Arg-Trp-Lys]-NH₂ (SEQ ID NO: 36)
Ac-Ser-Asn-Ser-Nle-c[Glu-Hyp-D-Phe-Arg-Trp-Lys]-NH₂ (SEQ ID NO: 37)
Ac-D-Ser-Asn-Ser-Nle-c[Glu-Hyp-D-Phe-Arg-Trp-Lys]-NH₂ (SEQ ID NO: 38)
Ac-Ser-Tyr-Hyp-Nle-c[Glu-Hyp-D-Phe-Arg-Trp-Lys]-NH₂ (SEQ ID NO: 39)
Ac-D-Ser-Tyr-Hyp-Nle-c[Glu-Hyp-D-Phe-Arg-Trp-Lys]-NH₂ (SEQ ID NO: 40)
Ac-Ser-His-Hyp-Nle-c[Glu-Hyp-D-Phe-Arg-Trp-Lys]-NH₂ (SEQ ID NO: 41)
Ac-Gln-His-Hyp-Nle-c[Glu-Hyp-D-Phe-Arg-Trp-Lys]-NH₂ (SEQ ID NO: 42)
Ac-Gln-Arg-Hyp-Nle-c[Glu-Hyp-D-Phe-Arg-Trp-Lys]-NH₂ (SEQ ID NO: 43)
Ac-Asn-Arg-Hyp-Nle-c[Glu-Hyp-D-Phe-Arg-Trp-Lys]-NH₂ (SEQ ID NO: 44)
Ac-Asn-homoArg-Hyp-Nle-c[Glu-Hyp-D-Phe-Arg-Trp-Lys]-NH₂ (SEQ ID NO: 45)
Ac-D-Ser-Asn-Hyp-Nle-c[Glu-Hyp-D-Phe-Arg-Trp-Lys]-NH₂ (SEQ ID NO: 46)
Ac-Gln-Tyr-Pro-Nle-c[Glu-Hyp-D-Phe-Arg-Trp-Lys]-NH₂ (SEQ ID NO: 47)
Ac-Ser-His-Pro-Nle-c[Glu-Hyp-D-Phe-Arg-Trp-Lys]-NH₂ (SEQ ID NO: 48)
Ac-Asn-His-Pro-Nle-c[Glu-Hyp-D-Phe-Arg-Trp-Lys]-NH₂ (SEQ ID NO: 49)
Ac-Ser-Arg-Pro-Nle-c[Glu-Hyp-D-Phe-Arg-Trp-Lys]-NH₂ (SEQ ID NO: 50)
Ac-D-Ser-Arg-Pro-Nle-c[Glu-Hyp-D-Phe-Arg-Trp-Lys]-NH₂ (SEQ ID NO: 51)
Ac-Ser-homoArg-Pro-Nle-c[Glu-Hyp-D-Phe-Arg-Trp-Lys]-NH₂ (SEQ ID NO: 52)
Ac-D-Ser-homoArg-Pro-Nle-c[Glu-Hyp-D-Phe-Arg-Trp-Lys]-NH₂ (SEQ ID NO: 53)
Ac-Gln-Asn-Pro-Nle-c[Glu-Hyp-D-Phe-Arg-Trp-Lys]-NH₂ (SEQ ID NO: 54)
Ac-Asn-Asn-Pro-Nle-c[Glu-Hyp-D-Phe-Arg-Trp-Lys]-NH₂ (SEQ ID NO: 55)
Ac-Ser-Tyr-Thr-Nle-c[Glu-Hyp-D-Phe-Arg-Trp-Lys]-NH₂ (SEQ ID NO: 56)
Ac-D-Ser-His-Thr-Nle-c[Glu-Hyp-D-Phe-Arg-Trp-Lys]-NH₂ (SEQ ID NO: 57)
Ac-Gln-His-Thr-Nle-c[Glu-Hyp-D-Phe-Arg-Trp-Lys]-NH₂ (SEQ ID NO: 58)
Ac-Ser-Arg-Thr-Nle-c[Glu-Hyp-D-Phe-Arg-Trp-Lys]-NH₂ (SEQ ID NO: 59)
Ac-D-Ser-Arg-Thr-Nle-c[Glu-Hyp-D-Phe-Arg-Trp-Lys]-NH₂ (SEQ ID NO: 60)
Ac-Ser-homoArg-Thr-Nle-c[Glu-Hyp-D-Phe-Arg-Trp-Lys]-NH₂ (SEQ ID NO: 61)
Ac-Asn-homoArg-Thr-Nle-c[Glu-Hyp-D-Phe-Arg-Trp-Lys]-NH₂ (SEQ ID NO: 62)
Ac-Gln-Asn-Thr-Nle-c[Glu-Hyp-D-Phe-Arg-Trp-Lys]-NH₂ (SEQ ID NO: 63)
Ac-Asn-Asn-Thr-Nle-c[Glu-Hyp-D-Phe-Arg-Trp-Lys]-NH₂ (SEQ ID NO: 64)
Ac-D-Ser-Tyr-Gly-Nle-c[Glu-Hyp-D-Phe-Arg-Trp-Lys]-NH₂ (SEQ ID NO: 65)
Ac-Gln-Tyr-Gly-Nle-c[Glu-Hyp-D-Phe-Arg-Trp-Lys]-NH₂ (SEQ ID NO: 66)
Ac-Ser-His-Gly-Nle-c[Glu-Hyp-D-Phe-Arg-Trp-Lys]-NH₂ (SEQ ID NO: 67)
Ac-Asn-His-Gly-Nle-c[Glu-Hyp-D-Phe-Arg-Trp-Lys]-NH₂ (SEQ ID NO: 68)
Ac-Ser-Arg-Gly-Nle-c[Glu-Hyp-D-Phe-Arg-Trp-Lys]-NH₂ (SEQ ID NO: 69)
Ac-Asn-Arg-Gly-Nle-c[Glu-Hyp-D-Phe-Arg-Trp-Lys]-NH₂ (SEQ ID NO: 70)
Ac-D-Ser-homoArg-Gly-Nle-c[Glu-Hyp-D-Phe-Arg-Trp-Lys]-NH₂ (SEQ ID NO: 71)
Ac-Gln-homoArg-Gly-Nle-c[Glu-Hyp-D-Phe-Arg-Trp-Lys]-NH₂ (SEQ ID NO: 72)
Ac-Ser-Asn-Gly-Nle-c[Glu-Hyp-D-Phe-Arg-Trp-Lys]-NH₂ (SEQ ID NO: 73)
Ac-Ser-Tyr-Ser-Nle-c[Glu-Hyp-D-Phe-Arg-Trp-Lys]-NH₂ (SEQ ID NO: 74)
Ac-Ser-His-Ser-Nle-c[Glu-Hyp-D-Phe-Arg-Trp-Lys]-NH₂ (SEQ ID NO: 75)
Ac-Ser-Arg-Ser-Nle-c[Glu-Hyp-D-Phe-Arg-Trp-Lys]-NH₂ (SEQ ID NO: 76)
Ac-Ser-His-Ser-Nle-c[Asp-Hyp-D-Phe-Arg-Trp-Lys]-NH₂ (SEQ ID NO: 77)
Ac-Ser-His-Ser-Nle-c[Glu-Ser-D-Phe-Arg-Trp-Lys]-NH₂ (SEQ ID NO: 78)
Ac-Ser-His-Ser-Nle-c[Glu-Hyp-D-Phe(3-trifluoromethyl)-Arg-Trp-Lys]-NH₂ (SEQ ID NO: 79)
Ac-Ser-His-Ser-Nle-c[Glu-Hyp-D-Phe(2-methyl)-Arg-Trp-Lys]-NH₂ (SEQ ID NO: 80)
Ac-Ser-His-Ser-Nle-c[Glu-Hyp-D-Phe(2-chloro)-Arg-Trp-Lys]-NH₂ (SEQ ID NO: 81)
Ac-Nle-c[Asp-Thr-D-Phe-Arg-Trp-Lys]-NH₂ (SEQ ID NO: 82)
Ac-Nle-c[Asp-Dap-D-Phe-Arg-Trp-Lys]-NH₂ (SEQ ID NO: 83)
Ac-Nle-c[Asp-(4-thiazolyl)Ala-D-Phe-Arg-Trp-Lys]-NH₂ (SEQ ID NO: 84)
Ac-Nle-c[Asp-Phe(4-amino)-D-Phe-Arg-Trp-Lys]-NH₂ (SEQ ID NO: 85)
Ac-Nle-c[Asp-Cit-D-Phe-Arg-Trp-Lys]-NH₂ (SEQ ID NO: 86)
Ac-Ser-His-Ser-Nle-c[Asp-(4-thiazolyl)Ala-D-Phe-Arg-Trp-Lys]-NH₂ (SEQ ID NO: 87).

Other embodiments of the invention are clear from the claims.

In one embodiment of the present invention, the compound is an agonist of a melanocortin receptor.

In one embodiment of the present invention, the compound is an MC4 agonist.

In one embodiment of the present invention, the compound is a selective MC4 agonist. In this context, selectivity is to be understood in relation to the activity of the compound with respect to MC1, MC3 and/or MC5. If a compound is a significantly more potent MC4 agonist than it is a potent MC1, MC3 and/or MC5 agonist, it is deemed to be a selective MC4 agonist. The potencies of a compound with respect to MC1 and MC4 are determined in receptor binding assays as described in assay IV (MC 1) and assay V (MC4). If a compound is more than 10 times, such as more than 50 times, such as more than 100 times more potent with respect to MC4 than with respect to MC1, it is deemed to be a selective MC4 agonist with respect to MC1. The potencies of a compound with respect to MC3, MC4 and MC5 are determined in functional assays as described in assay II (MC 3 and MC5) and assay III (MC4). If a compound is more than 10 times, such as more than 50 times, such as more than 100 times more potent with respect to MC4 than with respect to MC3, it is deemed to be a selective MC4 agonist with respect to MC3. If a compound is more than 10 times, such as more than 50 times, such as more than 100 times more potent with respect to MC4 than with respect to MC5, it is deemed to be a selective MC4 agonist with respect to MC5. In a particular embodiment, the compound of the present invention is a selective MC4 agonist with respect to MC1, with respect to MC3, with respect to MC5, with respect to MC1 and MC3, with respect to MC1 and MC5, with respect to MC3 and MC5 or with respect to MC1, MC3 and MC5.

In one embodiment, the compound of the present invention is a selective MC4 agonists and a MC3 antagonist. In this context, a compound is deemed to be a selective MC4 agonist and a MC3 antagonist if it is a selective MC4 agonist with respect to MC1 and MC5 as discussed above, and it antagonizes MC 3 measured as described in assay II. A compound with an $IC_{50}$ value less than 100 nM, such as less than 10 nM, such as less than 5 nM, such as less than 1 nM is deem to be a MC3 antagonist.

In one embodiment, the compound of the present invention is both a selective MC3 agonist and a selective MC4 agonist. In this context, a compound is deemed to be a selective MC3 and MC4 agonist if it is significantly more potent MC3 and MC4 agonist than it is a potent MC1 and MC5 agonist. The selectivity of a compound with respect to MC1 and MC3 are determined by comparing the potency determined for MC1 as described in assay IV with the potency for MC3 determined as described in assay II. If a compound is more than 10 times, such as more than 50 times, such as more than 100 times more potent with respect to MC3 than with respect to MC1 it is deemed to be a selective MC3 agonist with respect to MC1. The selectivity of compound with respect to MC3 and MC5 are determined by comparing the potency determined as described in assay II. If a compound is more than 10 times, such as more the 50 times, such as more than 100 times more potent with respect to MC3 than with respect to MC5 it is deemed to a selective MC3 agonist with respect to MC5 receptor. The MC4 selectivity of a compound with respect to MC3 and MC5 is determined as discussed above.

Compounds of the present invention modulate melanocortine receptors, and they are therefore believed to be particularly suited for the treatment of diseases or states which can be treated by a modulation of the melanocortine receptor activity. In particular, compounds of the present invention are believed to be suited for the treatment of diseases or states by activating the MC4 receptor.

In one embodiment, the present invention provides a method of delaying the progression from IGT to type 2 diabetes, the method comprising administering to a patient in need thereof an effective amount of a compound of the present invention.

In one embodiment, the present invention provides a method of delaying the progression from type 2 diabetes to insulin requiring diabetes, the method comprising administering to a patient in need thereof an effective amount of a compound of the present invention.

In one embodiment, the invention relates to a method of treating obesity or preventing overweight, the method comprising administering to a patient in need thereof an effective amount of a compound of the present invention.

In one embodiment, the present invention provides a method of regulating the appetite, the method comprising administering to a patient in need thereof an effective amount of a compound of the present invention.

In one embodiment, the invention relates to a method of inducing satiety, the method comprising administering to a patient in need thereof an effective amount of a compound of the present invention.

In one embodiment, the invention relates to a method of preventing weight regain after successfully having lost weight.

In one embodiment, the invention relates to a method of preventing weight gain, the method comprising administering to a patient in need thereof an effective amount of a compound of the present invention.

In one embodiment, the invention relates to a method of increasing energy expenditure.

In one embodiment, the present invention provides a method of treating a disease or state related to overweight or obesity, the method comprising administering to a patient in need thereof an effective amount of a compound of the present invention.

In one embodiment, the invention relates to a method of treating bulimia, the method comprising administering to a patient in need thereof an effective amount of a compound of the present invention.

In one embodiment, the invention relates to a method of treating a disease or state selected from atherosclerosis, hypertension, diabetes, type 2 diabetes, impaired glucose tolerance (IGT), dyspilidemia, coronary heart disease, gallbladder disease, gall stone, osteoarthritis, cancer, sexual dysfunction and the risk of premature death, the method comprising administering to a patient in need thereof an effective amount of a compound of the present invention.

In particular, compounds of the present invention may be suited for the treatment of diseases in obese or overweight patients. Accordingly, the present invention also provides a method of treating in obese patients diseases or states selected from amongst type 2 diabetes, impaired glucose tolerance (IGT), dyspilidemia, coronary heart disease, gallbladder disease, gall stone, osteoarthritis, cancer, sexual dysfunction and the risk of premature death in obese patients, the method comprising administering to a patient in need thereof an effective amount of a compound of the present invention.

In addition, MC4 agonists could have a positive effect on insulin sensitivity, drug abuse by modulating the reward system, haemorhegic shock. Furthermore, MC3 and MC4 agonist have antipyretic effects and both have been suggested to be involved in peripheral nerve regeneration and the MC4 receptor is also known to reduce stress response.

In all therapeutic method disclosed above, the compound of the present invention may be administered alone. However, it may also be administered in combination with one or more additional therapeutically active compounds, either sequentially or concomitantly.

In one aspect, the invention relates to a pharmaceutical composition comprising a compound of the present invention, optionally in combination with one or more additional therapeutically active compound together with one or more pharmaceutically acceptable carrier or exipient in unit dosage form comprising about 0.05 mg to about 1000 mg, such as about 0.1 mg to about 500 mg, such as from about 0.5 mg to about 200 mg of a compound of the present invention.

The present invention also relates to the use of a compound of the present invention in the manufacture of a medicament for the treatment of diseases or states selected from overweight or obesity, bulimia, atherosclerosis, hypertension, type 2 diabetes, impaired glucose tolerance (IGT), dyspilidemia, coronary heart disease, gallbladder disease, gall stone, osteoarthritis, cancer, sexual dysfunction and the risk of premature death The present invention also relates to the use of a compound of the present invention, alone or in combination with an additional therapeutically active compound, in the manufacture of a medicament effective in delaying the progression from IGT to type 2 diabetes, delaying the progression from type 2 diabetes to insulin requiring diabetes, regulating the appetite, inducing satiety, preventing weight gain after successfully having lost weight or increasing energy expenditure.

As described above, compounds of the present invention may be administered or applied in combination with one or more additional therapeutically active compound. Suitable additional compounds may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon-like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic Pcells e.g. potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, glucokinase activators, such as those described in WO 02/08209 to Hoffmann La Roche, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferator-activated receptor) and RXR (retinoid X receptor) agonists such as ALRT-268, LG-1268 or LG-1069.

Other examples of suitable additional therapeutically active compounds include insulin or insulin analogues, sulfonylurea e.g. tolbutamide, chlorpropamide, tolazamide, glibenclamide, glipizide, glimepiride, glicazide, glyburide, biguanide e.g. metformin, meglitinide e.g. repaglinide or senaglinide/nateglinide.

Other examples of suitable additional therapeutically active compounds include thiazolidinedione insulin sensitizer e.g. troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

Other examples of suitable additional therapeutically active compounds include insulin sensitizer e.g. such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

Other examples of suitable additional therapeutically active compounds include α-glucosidase inhibitor e.g. voglibose, emiglitate, miglitol or acarbose.

Other examples of suitable additional therapeutically active compounds include glycogen phosphorylase inhibitor e.g. the compounds described in WO 97/09040 (Novo Nordisk A/S).

Other examples of suitable additional therapeutically active compounds include a glucokinase activator.

Other examples of suitable additional therapeutically active compounds include an agent acting on the ATP-dependent potassium channel of the pancreatic β-cells e.g. tolbutamide, glibenclamide, glipizide, glicazide, BTS-67582 or repaglinide.

Other examples of suitable additional therapeutically active compounds include nateglinide.

Other examples of suitable additional therapeutically active compounds include an antihyperlipidemic agent or a antilipidemic agent e.g. cholestyramine, colestipol, clofibrate, gemfibrozil, lovastatin, pravastatin, simvastatin, probucol or dextrothyroxine.

Other examples of said additional therapeutically active compounds include antiobesity compounds or appetite regulating agents. Such compounds may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, chemical uncouplers, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists and ciliary neurotrophic factor. Further antiobesity agents are bupropion (antidepressant), topiramate (anticonvulsant), ecopipam (dopamine D1/D5 antagonist), naltrexone (opioid antagonist), and peptide $YY_{3-36}$ (Batterham et al, Nature 418, 650-654 (2002)).

In one embodiment, the antiobesity agent is leptin.

In one embodiment, the antiobesity agent is peptide $YY_{3-36}$.

In one embodiment, the antiobesity agent is a serotonin and norepinephrine reuptake inhibitor e.g. sibutramine.

In one embodiment, the antiobesity agent is a lipase inhibitor e.g. orlistat.

In one embodiment, the antiobesity agent is an adrenergic CNS stimulating agent e.g. dexamphetamine, amphetamine, phentermine, mazindol phendimetrazine, diethylpropion, fenfluramine or dexfenfluramine.

Other examples of suitable additional therapeutically active compounds include antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin.

In one embodiment of the uses and methods of the present invention, the compound of the present invention may be administered or applied in combination with more than one of the above-mentioned compounds e.g. in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds for use according to the present invention may be administered alone or in combination with pharmaceutically acceptable carriers or excipients, in either single or multiple doses. The pharmaceutical compositions according to the present invention may be formulated with pharmaceutically acceptable carriers or diluents as well as any other known adjuvants and excipients in accordance with conventional techniques such as those disclosed in Remington: The Science and Practice of Pharmacy, 20$^{th}$ Edition, Gennaro, Ed., Mack Publishing Co., Easton, Pa., 2000.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

It has been established that many MT-II analogues exhibit a short half life, and that the effect of the compounds thus disappears rather quickly after administration. This problem may be circumvented using dosing regimes with shorter dosing intervals or even dosing regimes with no intervals, i.e. continuous dosing, or dosing regimes characterised by periods of continuous dosing interrupted by periods of no dosing.

Various pumps and devices are known in the art which are useful for continuous or interrupted continuous dosing. In its simplest form, a reservoir containing a drug presented in a useful form is placed so that gravity, optionally via a valve whereby to control the flow, forces said drug into a subject via a needle or similar device which has penetrated the outer skin to allow a subcutaneous, intradermal or intravenous administration. It is also known to use pumps rather than gravity to supply the required force. Such pumps may be external pumps, or they may together with a reservoir by implanted in a subject. Pumps as described here may be carried by the subject and the flow from the pump may be adjusted individually to optimise the effect, taking the drug at hand and the subject to be treated into consideration.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres and nanoparticles.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. As discussed above, it is envisaged that continuous or interrupted continuous administration may be advantageous. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds for use according to the present invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds for use according to the present invention which are generally prepared by reacting the free base with a suitable organic or inorganic acid or by reacting the acid with a suitable organic or inorganic base. When a compound for use according to the present invention, such as a compound of Formula (I), contains a free base such salts are prepared in a conventional manner by treating a solution or suspension of the compound with a chemical equivalent of a pharmaceutically acceptable acid. When a compounds for use according to the present invention, such as a compound of Formula (I), contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds for use according to the present invention and these form a further aspect of the present invention.

For parenteral administration, solutions of the compounds for use according to the present invention in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compounds for use according to the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavouring agents, colouring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatine or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatine capsules where the active ingredient is mixed with an inert solid diluent, for example, calcium carbonate, calcium phosphate or kaolin, or a soft gelatine capsule wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexagon such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more colouring agents, one or more flavouring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavouring, and colouring agents may also be present.

The pharmaceutical compositions comprising a compound for use according to the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds for use according to the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds for use according to the present invention may form solvates with water or common organic solvents. Such solvates are also encompassed within the scope of the present invention.

Thus, in a further embodiment, there is provided a pharmaceutical composition comprising a compound for use according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

EXAMPLES

All compounds of the present can be synthesized by those skilled in the art using standard coupling and deprotection steps. A description of all necessary tools and synthetic methods can be found in "The Fine Art Of Solid Phase Synthesis", 2002/3 Catalog, Novabiochem.

A typical example which includes a cyclization step is as follows:

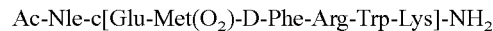

Ac-Nle-c[Glu-Met(O$_2$)-D-Phe-Arg-Trp-Lys]-NH$_2$ 1.a The protected peptidyl resin H-Nle-Glu(OPip)-Met(O$_2$)-D-Phe-Arg(Pmc)-Trp(Boc)-Lys(Mtt)-(Rink resin) was synthesized according to the Fmoc strategy on an Applied Biosystems 431A peptide synthesizer in 0.25 mmol scale using the manufacturer supplied FastMoc UV protocols which employ HBTU (2-(1H-Benzotriazol-1-yl-)-1,1,3,3 tetramethyluronium hexafluorophosphate) mediated couplings in NMP (N-methyl pyrrolidone) and UV monitoring of the deprotection of the Fmoc protection group. The starting resin used for the synthesis was 0.50 g (4-((2',4'-dimethoxyphenyl)-(Fmoc-amino)methyl)-phenoxy resin (Rink resin) (Novabiochem) with a loading of 0.51 mmol/g. The protected amino acid derivatives used were Fmoc-Nle-OH, Fmoc-D-Phe-OH, Fmoc-Arg(Pmc)-OH, Fmoc-Lys(Mtt)-OH, Fmoc-Trp(Boc)-OH, Fmoc-Glu(OPip)-OH, Fmoc-Met(O$_2$)-OH.

1.b Then the peptide resin resulting from (1.a) was acylated with a preactivated solution of acetic acid (1.0 mmol), HODhbt (3,4-dihydro-3-hydroxy-4-oxo-1,2,3-benzotriazine) (1.0 mmol), DIC (diisopropyl carbodiimide) (1.0 mmol), DIEA (N,N-Diisopropylethylamine) (0.25 mmol), NMP 5 ml. After 2 hours at room temperature the resin was filtered and washed with NMP and DCM (dichlormethane).

1.c The resin resulting from (1.b) was treated with 5×10 ml 2% TFA (trifluoroacetic acid), 2% TES (triethylsilane) in DCM during 60 min. with regular mixing. The resin was washed with NMP, NMP with 5% DIEA and NMP. The peptide was cyclized using HODhbt (1.0 mmol), PyBOP ((benzotriazol-1-yloxy)tripyrrolidinophosphonium hexafluorophosphate 1H-benzotriazol-1-yloxy-tripyrrolidinophosphonium hexafluorophosphate) ) (1.0 mmol) and DIEA (2.0 mmol) in NMP 5 mL with regular mixing for 4 h. The resin was washed with NMP and DCM.

1.d The peptide was cleaved from protected peptidyl resin obtained from (1.c) by stirring for 60 min at room temperature with 10 mL 2.5% water, 2.5% TES in TFA. The cleavage mixture was filtered and the filtrate was concentrated to approximately 1 ml by a stream of nitrogen. The crude peptide was precipitated from this oil with 50 ml diethyl ether and washed 3 times with 50 ml diethyl ether.

The crude cyclic peptide was purified by preparative RP-HPLC. For analytical data, see example 4 below.

In the examples listed below, Rt values are retention times and the mass values are those detected by the MS detector obtained by using one of the following LC/MS devices.

LC/MS system 1: Agilent 1100 Series, electrospray; column: Waters XTerra® $C_{18}$ 5 μm 3.0×50 mm; water/acetonitrile containing 0.05% TFA; gradient: 5%→100% acetonitrile from 0 to 6.75 min, elution until t=9.0 min; flow 1.5 ml/min LC/MS system 2: Sciex API-100 Quadrupole MS, electrospray; column: Waters XTerra® $C_{18}$ 5 μm 3.0×50 mm; water/acetonitrile containing 0.05% TFA; gradient: 5%→90% acetonitrile from 0 to 7.5 min, elution until t=10.0 min; flow 1.5 ml/min LC/MS system 3: Sciex API-150 Ex Quadrupole MS, electrospray; column: Waters XTerra® $C_{18}$ 5 μm 3.0×50 mm; water/acetonitrile containing 0.05% TFA; gradient: 5%→15% acetonitrile from 1.0 to 2.0 min, 15%→45% acetonitrile from 2.0 to 28.0 min, 45%→90% acetonitrile from 28.0 to 30.0 min, elution until t=30.0 min; flow 1.5 ml/min LC/MS system 4: as described for system 3, but with another gradient: 5%=20% acetonitrile from 1.0 to 3.0 min, 20%→50% acetonitrile from 3.0 to 16.0 min, 50%→90% acetonitrile from 16.0 to 18.0 min, elution until t=18.0 min Example 1

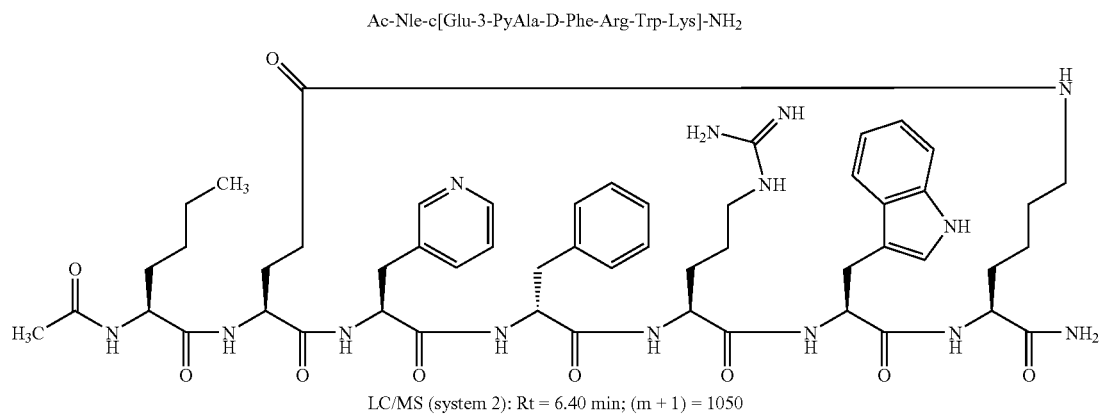

Ac-Nle-c[Glu-3-PyAla-D-Phe-Arg-Trp-Lys]-NH$_2$

LC/MS (system 2): Rt = 6.40 min; (m + 1) = 1050

Example 2

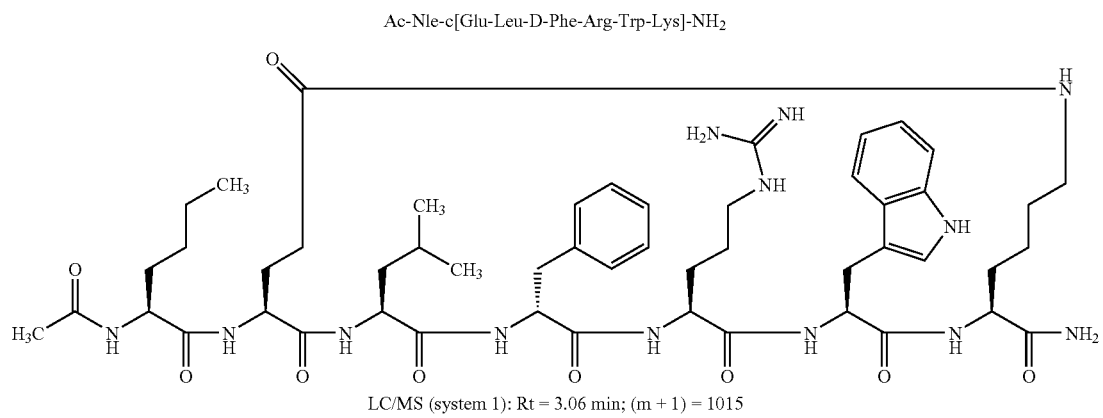

Ac-Nle-c[Glu-Leu-D-Phe-Arg-Trp-Lys]-NH$_2$

LC/MS (system 1): Rt = 3.06 min; (m + 1) = 1015

Example 3
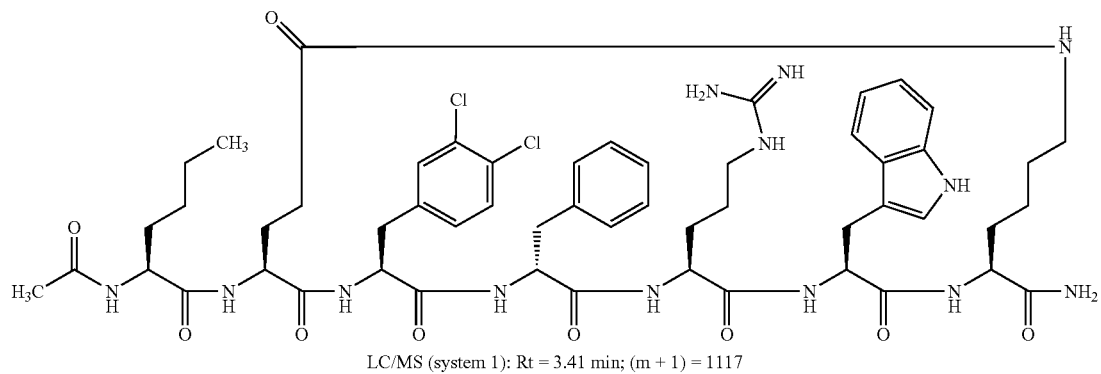
Ac-Nle-c[Glu-Phe(3,4-dichloro)-D-Phe-Arg-Trp-Lys]-NH$_2$
LC/MS (system 1): Rt = 3.41 min; (m + 1) = 1117
Example 4
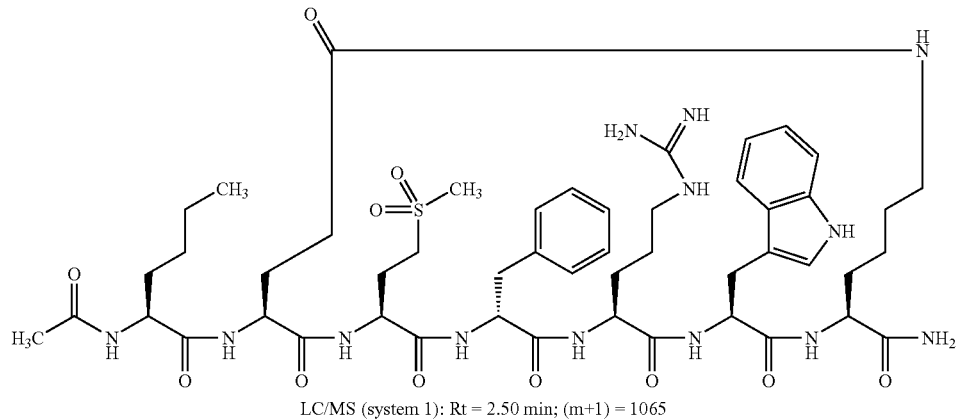
Ac-Nle-c[Glu-Met(O$_2$)-D-Phe-Arg-Trp-Lys]-NH$_2$
LC/MS (system 1): Rt = 2.50 min; (m+1) = 1065
Example 5
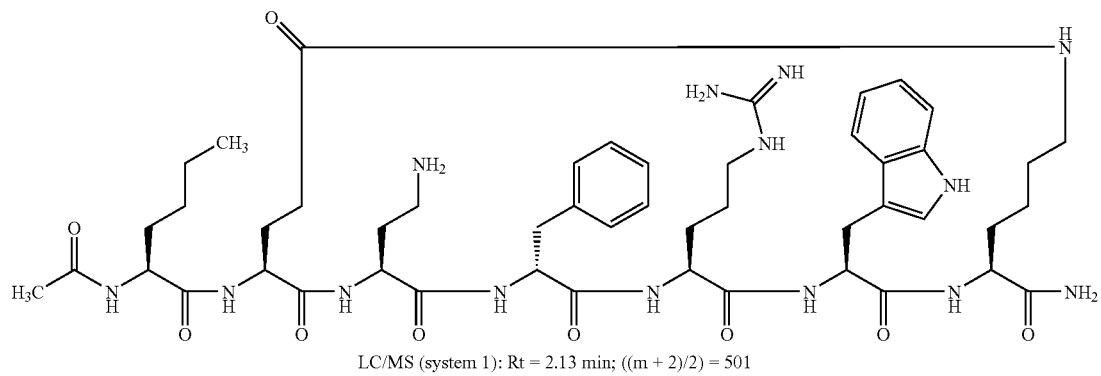
Ac-Nle-c[Glu-Dab-D-Phe-Arg-Trp-Lys]-NH$_2$
LC/MS (system 1): Rt = 2.13 min; ((m + 2)/2) = 501

Example 6
Ac-Nle-c[Glu-Cgl-D-Phe-Arg-Trp-Lys]-NH₂
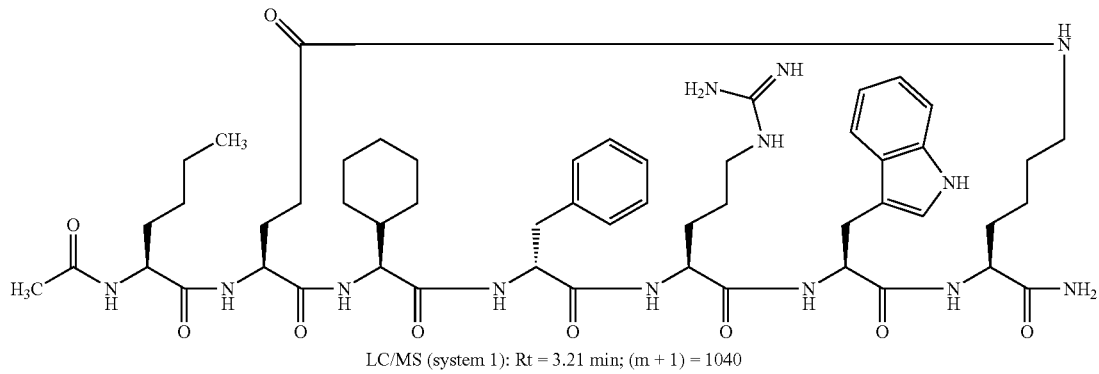
LC/MS (system 1): Rt = 3.21 min; (m + 1) = 1040
Example 7
Ac-Nle-c[Glu-Val-D-Phe-Arg-Trp-Lys]-NH₂
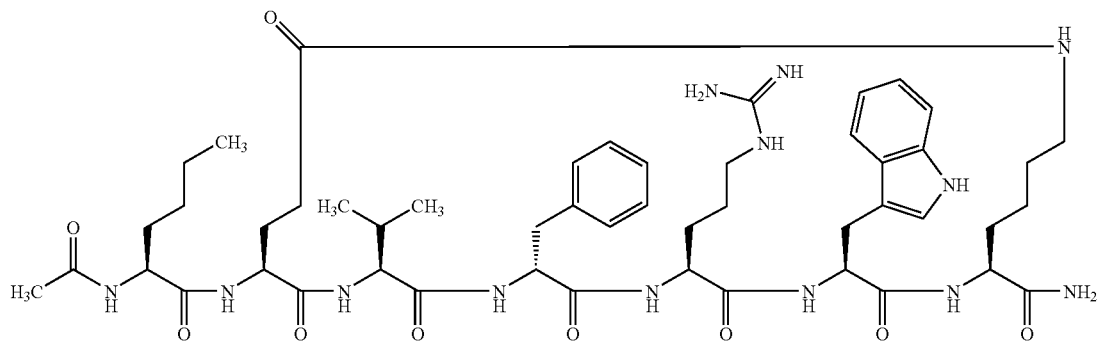
LC/MS (system 1): Rt = 2.69 min; (m + 1) = 1000
Example 8
Ac-Nle-c[Glu-Tic-D-Phe-Arg-Trp-Lys]-NH₂
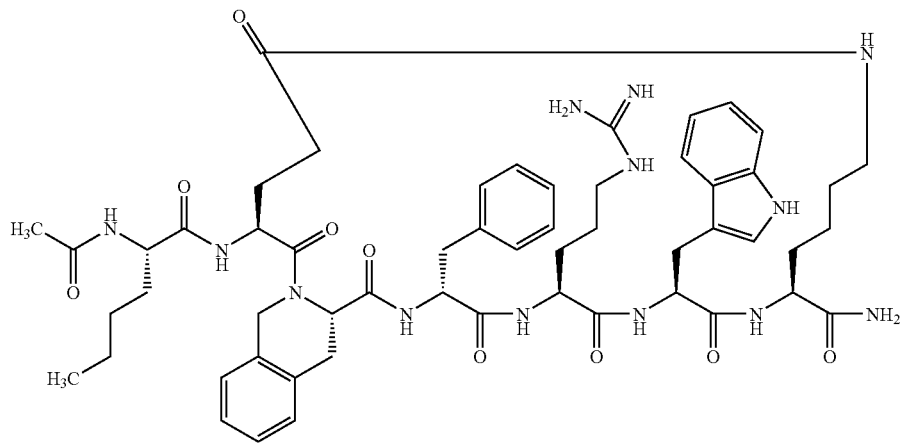
LC/MS (system 1): Rt = 2.88 min; (m+1) = 1061

Example 9
Ac-Nle-c[Glu-Cha-D-Phe-Arg-Trp-Lys]-NH₂
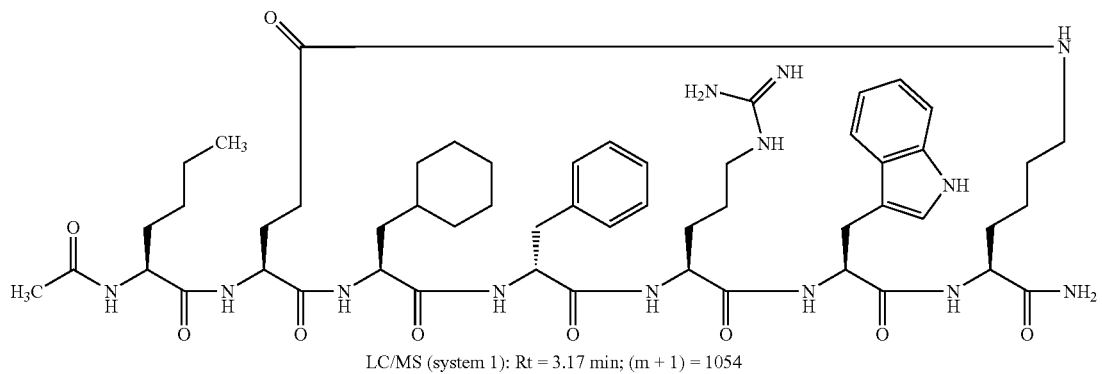
LC/MS (system 1): Rt = 3.17 min; (m + 1) = 1054
Example 10
Ac-Nle-c[Glu-Ile-D-Phe-Arg-Trp-Lys]-NH₂
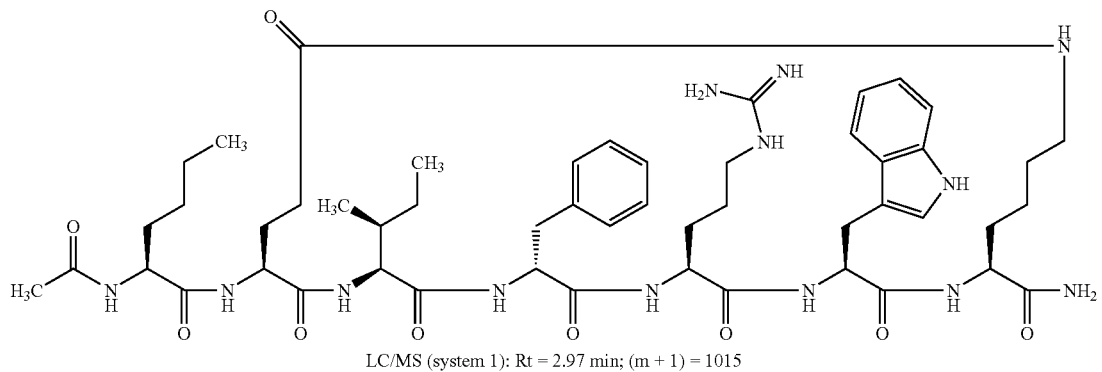
LC/MS (system 1): Rt = 2.97 min; (m + 1) = 1015
Example 11
Ac-Nle-c[Glu-tBuGly-D-Phe-Arg-Trp-Lys]-NH₂
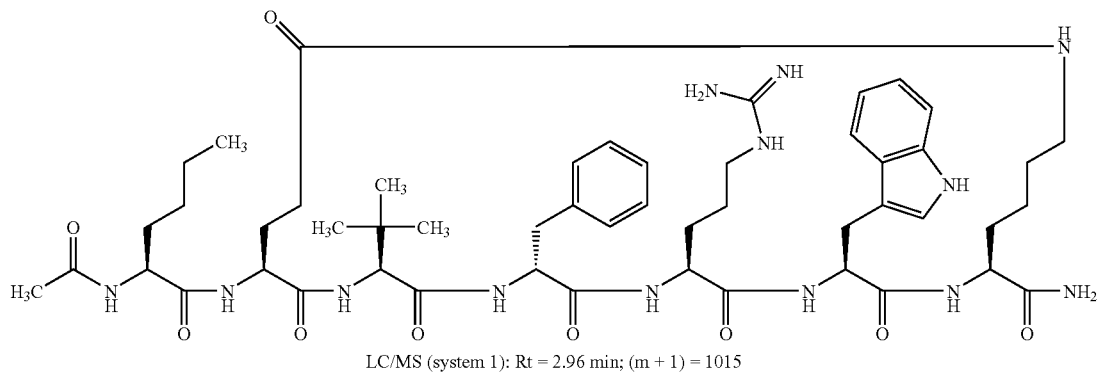
LC/MS (system 1): Rt = 2.96 min; (m + 1) = 1015

Example 12
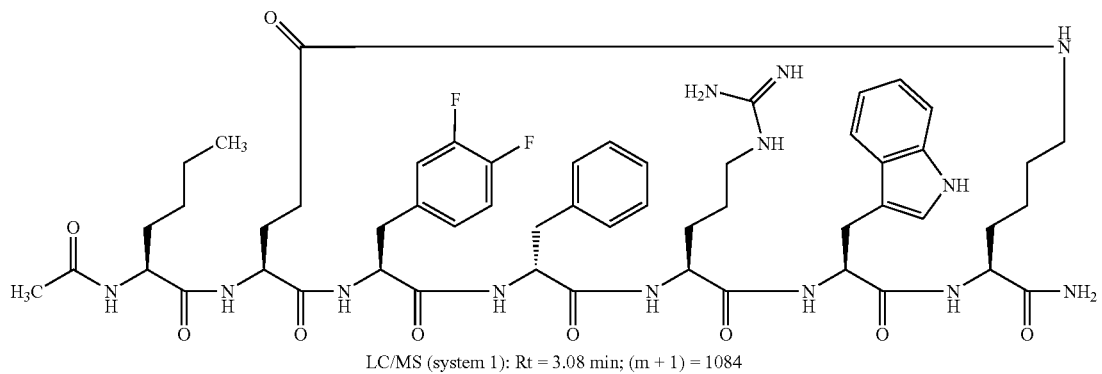
Ac-Nle-c[Glu-Phe(3,4-difluoro)-D-Phe-Arg-Trp-Lys]-NH₂
LC/MS (system 1): Rt = 3.08 min; (m + 1) = 1084
Example 13
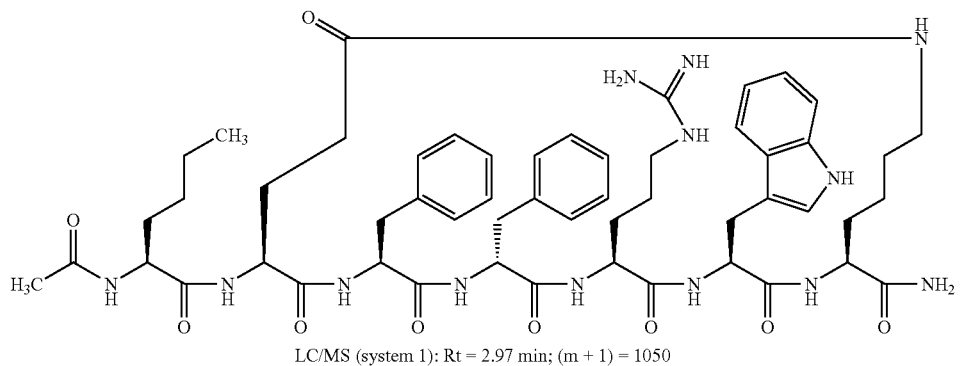
Ac-Nle-c[Glu-Phe-D-Phe-Arg-Trp-Lys]-NH₂
LC/MS (system 1): Rt = 2.97 min; (m + 1) = 1050
Example 14
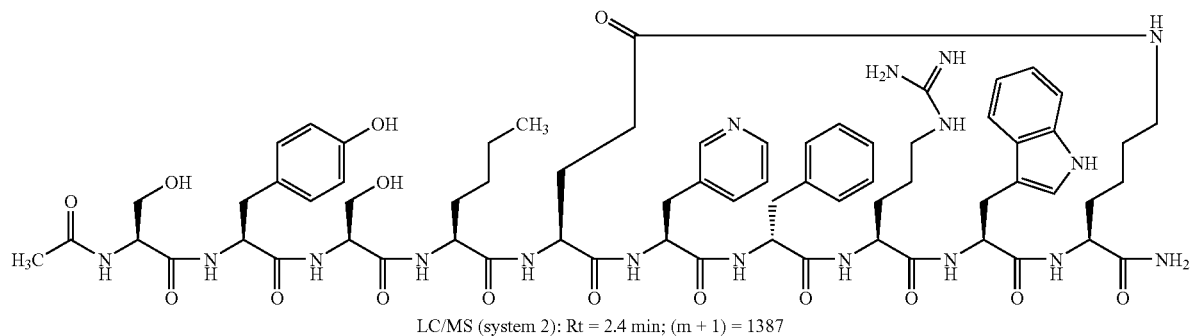
Ac-Ser-Tyr-Ser-Nle-c[Glu-3-PyAla-D-Phe-Arg-Trp-Lys]-NH₂
LC/MS (system 2): Rt = 2.4 min; (m + 1) = 1387

Example 15
H-Ala-Lys-Tyr-Ser-Nle-c[Glu-3-PyAla-D-Phe-Arg-Trp-Lys]-NH$_2$
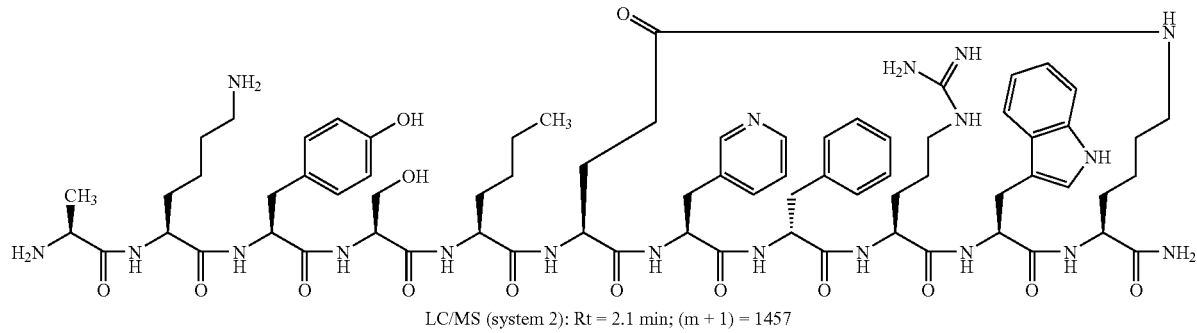
LC/MS (system 2): Rt = 2.1 min; (m + 1) = 1457
Example 16
2-Hydroxy-3-methylbutanoyl-Ser-Nle-c[Glu-3-PyAla-D-Phe-Arg-Trp-Lys]-NH$_2$
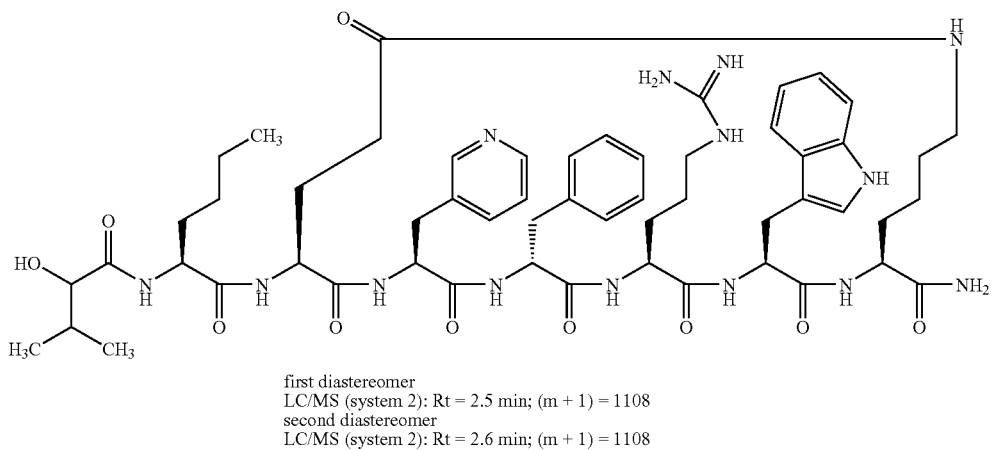
first diastereomer
LC/MS (system 2): Rt = 2.5 min; (m + 1) = 1108
second diastereomer
LC/MS (system 2): Rt = 2.6 min; (m + 1) = 1108
Example 17
H-Dab-Nle-c[Glu-3-PyAla-D-Phe-Arg-Trp-Lys]-NH$_2$
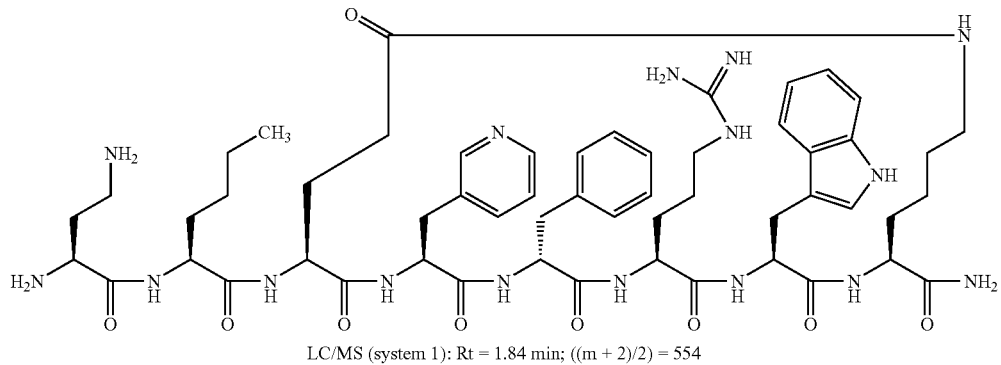
LC/MS (system 1): Rt = 1.84 min; ((m + 2)/2) = 554

Example 18
H-Ala-Lys-Ala-Nle-c[Glu-Hyp-D-Phe-Arg-Trp-Lys]-NH₂
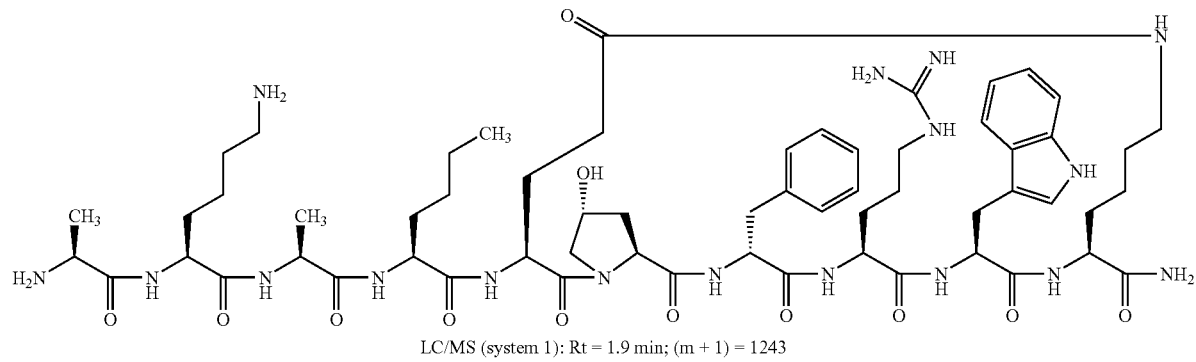
LC/MS (system 1): Rt = 1.9 min; (m + 1) = 1243
Example 19
Ac-Nle-c[Glu-Hyp-D-Phe(4-iodo)-Arg-Trp-Lys]-NH₂
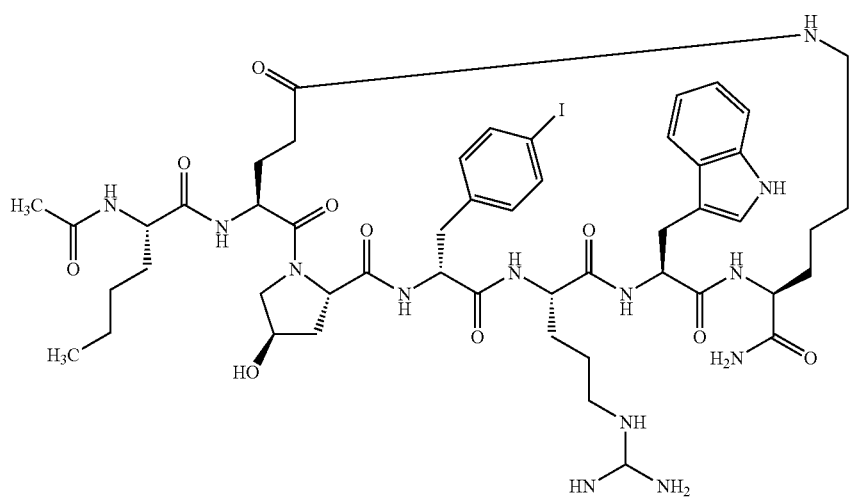
LC/MS (system 1): Rt = 2.73 min; (m+1) = 1140
Example 20
Hex-5-enoyl-Nle-c[Glu-Hyp-D-Phe-Arg-Trp-Lys]-NH₂
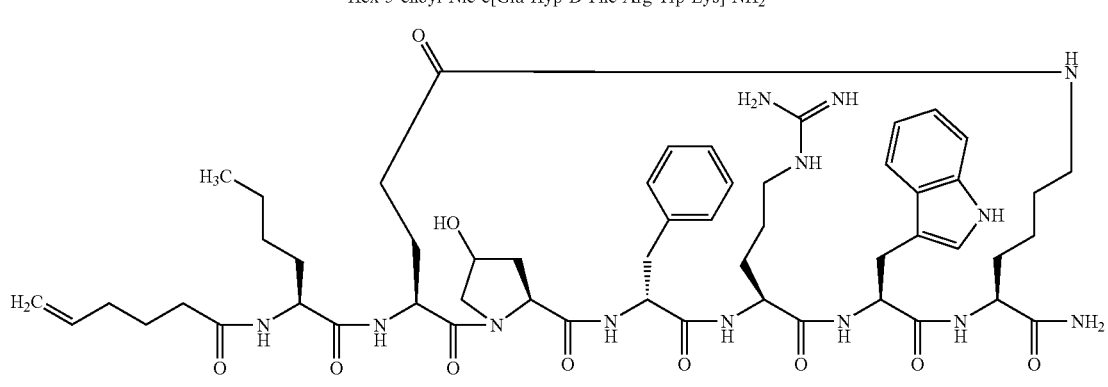
LC/MS (system 1): Rt = 2.92 min; ((m + 2)/2) = 534

Example 21
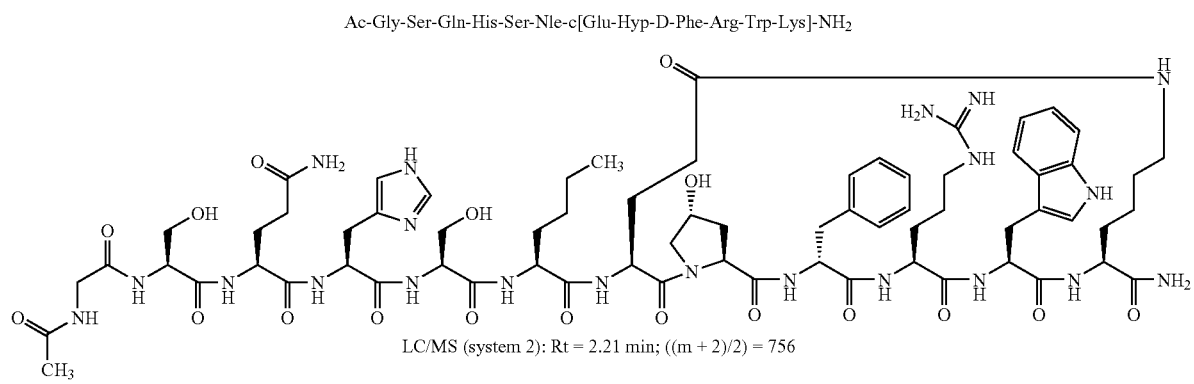
Ac-Gly-Ser-Gln-His-Ser-Nle-c[Glu-Hyp-D-Phe-Arg-Trp-Lys]-NH₂
LC/MS (system 2): Rt = 2.21 min; ((m + 2)/2) = 756
Example 22
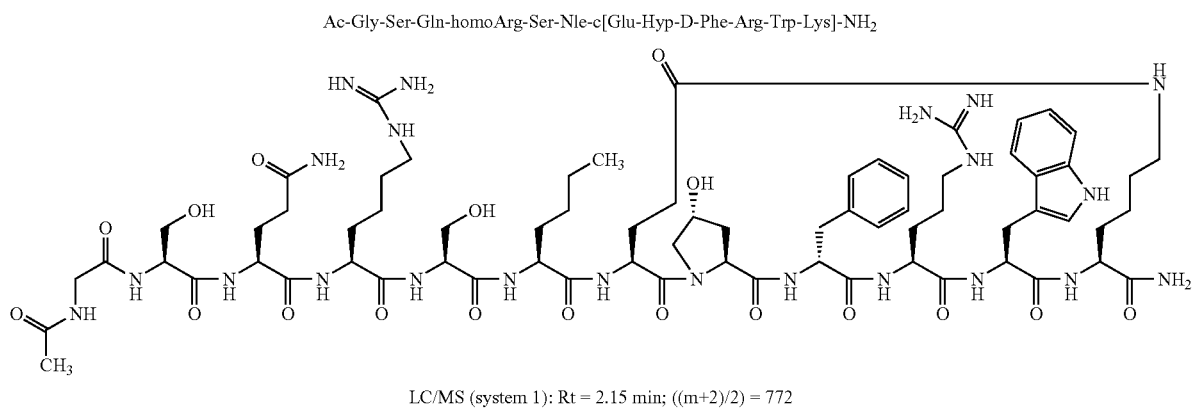
Ac-Gly-Ser-Gln-homoArg-Ser-Nle-c[Glu-Hyp-D-Phe-Arg-Trp-Lys]-NH₂
LC/MS (system 1): Rt = 2.15 min; ((m+2)/2) = 772
Example 23
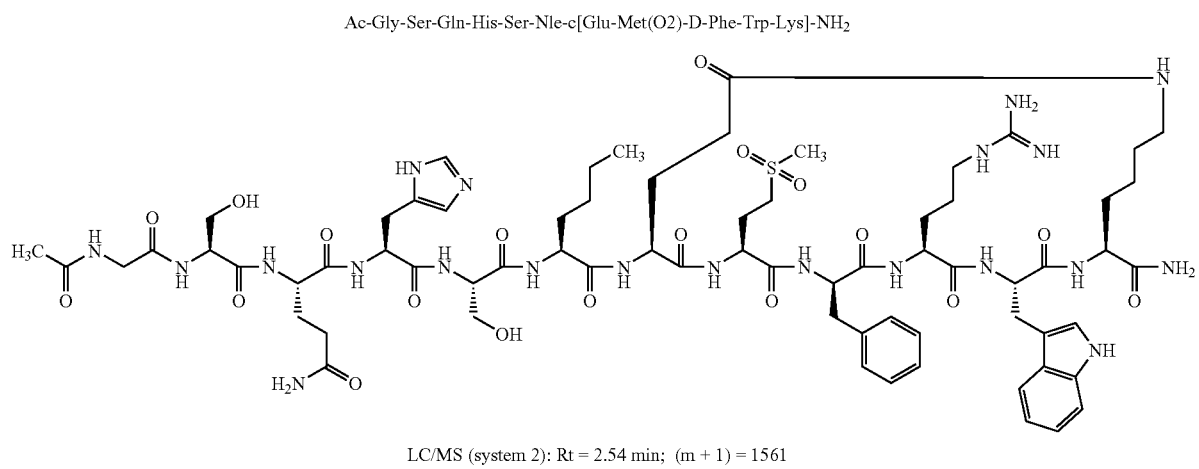
Ac-Gly-Ser-Gln-His-Ser-Nle-c[Glu-Met(O2)-D-Phe-Trp-Lys]-NH₂
LC/MS (system 2): Rt = 2.54 min; (m + 1) = 1561

Example 24
Ac-Nle-c[Glu-Hyp-D-Phe-Arg-Trp-Lys]-NH₂
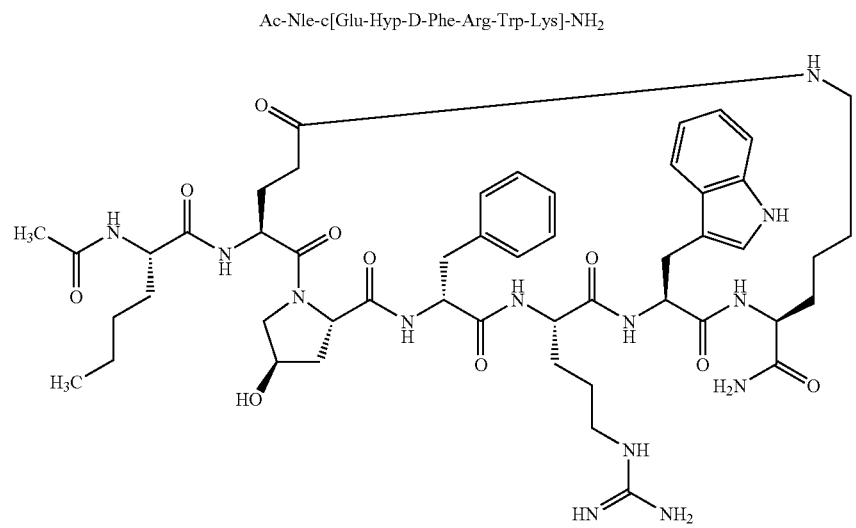
LC/MS (system 4): Rt = 5.66 min; (m + 1) = 1015
Example 25
Ac-Nle-c[Glu-Hyp-D-Phe-Arg-Trp-Lys]-(2-aminoethyl)amide
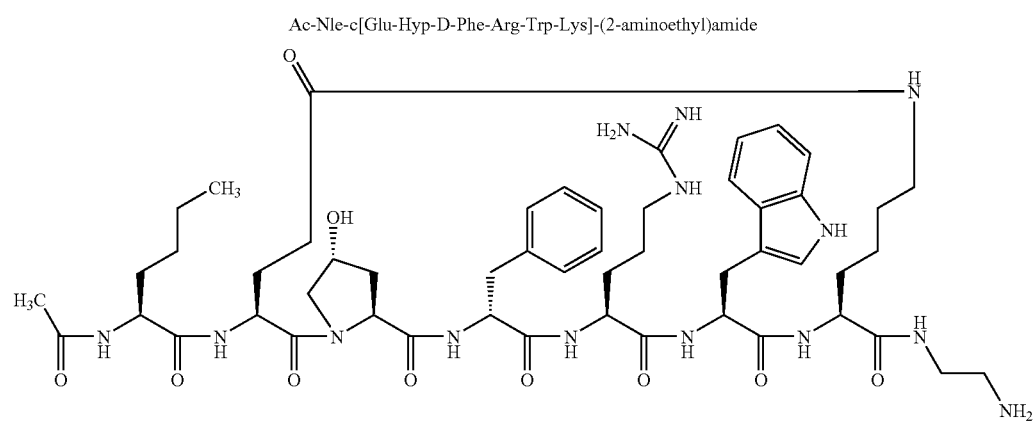
LC/MS (system 4): Rt = 4.71 min; ((m+2)/2) = 530

Example 26

Ac-Nle-c[Asp-Phe(4-amino)-D-Phe(4-chloro)-Arg-Trp-Lys]-NH₂

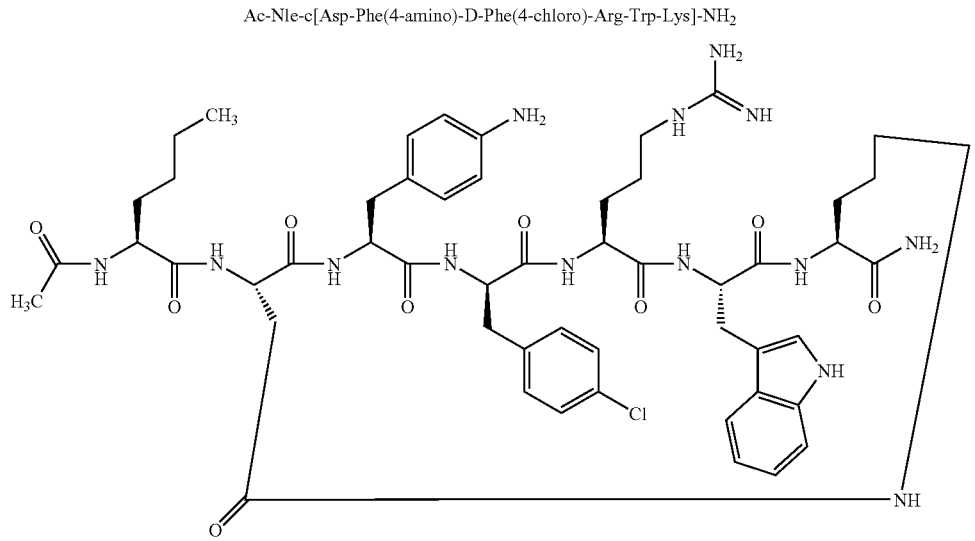

LC/MS (system 4): Rt = 3.3 min; ((m+2)/2) = 543

Example 27

Ac-Asn-Tyr-Ser-Nle-c[Glu-Hyp-D-Phe-Arg-Trp-Lys]-NH₂
LC/MS (system 3): Rt=8.46 min; ((m+2)/2)=690

Example 28

Ac-D-Ser-His-Ser-Nle-c[Glu-Hyp-D-Phe-Arg-Trp-Lys]-NH₂
LC/MS (system 3): Rt=5.60 min; ((m+2)/2)=664

Example 29

Ac-Gln-Arg-Ser-Nle-c[Glu-Hyp-D-Phe-Arg-Trp-Lys]-NH₂
LC/MS (system 3): Rt=5.51 min; ((m+2)/2)=694

Example 30

Ac-Ser-homoArg-Ser-Nle-c[Glu-Hyp-D-Phe-Arg-Trp-Lys]-NH₂
LC/MS (system 3): Rt=5.75 min; ((m+2)/2)=680

Example 31

Ac-Gln-homoArg-Ser-Nle-c[Glu-Hyp-D-Phe-Arg-Trp-Lys]-NH₂
LC/MS (system 3): Rt=5.62 min; ((m+2)/2)=700

Example 32

Ac-Ser-Asn-Ser-Nle-c[Glu-Hyp-D-Phe-Arg-Trp-Lys]-NH₂
LC/MS (system 3): Rt=6.87 min; (m+1)=651

Example 33

Ac-D-Ser-Asn-Ser-Nle-c[Glu-Hyp-D-Phe-Arg-Trp-Lys]-NH₂
LC/MS (system 3): Rt=6.88 min; (m+1)=652

Example 34

Ac-Ser-Tyr-Hyp-Nle-c[Glu-Hyp-D-Phe-Arg-Trp-Lys]-NH₂
LC/MS (system 3): Rt=8.11 min; ((m+2)/2)=690

Example 35

Ac-D-Ser-Tyr-Hyp-Nle-c[Glu-Hyp-D-Phe-Arg-Trp-Lys]-NH₂
LC/MS (system 3): Rt=8.24 min; ((m+2)/2)=690

Example 36

Ac-Ser-His-Hyp-Nle-c[Glu-Hyp-D-Phe-Arg-Trp-Lys]-NH₂
LC/MS (system 3): Rt=5.13 min; ((m+2)/2)=676

Example 37

Ac-Gln-His-Hyp-Nle-c[Glu-Hyp-D-Phe-Arg-Trp-Lys]-NH₂
LC/MS (system 3): Rt=5.16 min; ((m+2)/2)=697

Example 38

Ac-Gln-Arg-Hyp-Nle-c[Glu-Hyp-D-Phe-Arg-Trp-Lys]-NH₂
LC/MS (system 3): Rt=5.2 min; ((m+2)/2)=706

Example 39

Ac-Asn-Arg-Hyp-Nle-c[Glu-Hyp-D-Phe-Arg-Trp-Lys]-NH₂
LC/MS (system 3): Rt=5.13 min; ((m+2)/2)=699

Example 40

Ac-Asn-homoArg-Hyp-Nle-c[Glu-Hyp-D-Phe-Arg-Trp-Lys]-NH₂
LC/MS (system 3): Rt=5.47 min; ((m+2)/2)=707

Example 41

Ac-D-Ser-Asn-Hyp-Nle-c[Glu-Hyp-D-Phe-Arg-Trp-Lys]-NH$_2$
LC/MS (system 3): Rt=6.8 min; ((m+2)/2)=665

Example 42

Ac-Gln-Tyr-Pro-Nle-c[Glu-Hyp-D-Phe-Arg-Trp-Lys]-NH$_2$
LC/MS (system 3): Rt=9.06 min; ((m+2)/2)=702

Example 43

Ac-Ser-His-Pro-Nle-c[Glu-Hyp-D-Phe-Arg-Trp-Lys]-NH$_2$
LC/MS (system 3): Rt=5.7 min; ((m+2)/2)=669

Example 44

Ac-Asn-His-Pro-Nle-c[Glu-Hyp-D-Phe-Arg-Trp-Lys]-NH$_2$
LC/MS (system 3): Rt=5.59 min; ((m+2)/2)=682

Example 45

Ac-Ser-Arg-Pro-Nle-c[Glu-Hyp-D-Phe-Arg-Trp-Lys]-NH$_2$
LC/MS (system 3): Rt=5.92 min; ((m+2)/2)=678

Example 46

Ac-D-Ser-Arg-Pro-Nle-c[Glu-Hyp-D-Phe-Arg-Trp-Lys]-NH$_2$
LC/MS (system 3): Rt=5.93 min; ((m+2)/2)=678

Example 47

Ac-Ser-homoArg-Pro-Nle-c[Glu-Hyp-D-Phe-Arg-Trp-Lys]-NH$_2$
LC/MS (system 3): Rt=6.06 min; ((m+2)/2)=685

Example 48

Ac-D-Ser-homoArg-Pro-Nle-c[Glu-Hyp-D-Phe-Arg-Trp-Lys]-NH$_2$
LC/MS (system 3): Rt=6.13 min; ((m+2)/2)=685

Example 49

Ac-Gln-Asn-Pro-Nle-c[Glu-Hyp-D-Phe-Arg-Trp-Lys]-NH$_2$
LC/MS (system 3): Rt=7.85 min; ((m+2)/2)=677

Example 50

Ac-Asn-Asn-Pro-Nle-c[Glu-Hyp-D-Phe-Arg-Trp-Lys]-NH$_2$
LC/MS (system 3): Rt=8.03 min; ((m+2)/2)=671

Example 51

Ac-Ser-Tyr-Thr-Nle-c[Glu-Hyp-D-Phe-Arg-Trp-Lys]-NH$_2$
LC/MS (system 3): Rt=9.04 min; ((m+2)/2)=683

Example 52

Ac-D-Ser-His-Thr-Nle-c[Glu-Hyp-D-Phe-Arg-Trp-Lys]-NH$_2$
LC/MS (system 3): Rt=6.04 min; ((m+2)/2)=671

Example 53

Ac-Gln-His-Thr-Nle-c[Glu-Hyp-D-Phe-Arg-Trp-Lys]-NH$_2$
LC/MS (system 3): Rt=5.61 min; ((m+2)/2)=691

Example 54

Ac-Ser-Arg-Thr-Nle-c[Glu-Hyp-D-Phe-Arg-Trp-Lys]-NH$_2$
LC/MS (system 3): Rt=6.02 min; ((m+2)/2)=680

Example 55

Ac-D-Ser-Arg-Thr-Nle-c[Glu-Hyp-D-Phe-Arg-Trp-Lys]-NH$_2$
LC/MS (system 3): Rt=5.77 min; ((m+2)/2)=680

Example 56

Ac-Ser-homoArg-Thr-Nle-c[Glu-Hyp-D-Phe-Arg-Trp-Lys]-NH$_2$
LC/MS (system 3): Rt=5.99 min; ((m+2)/2)=687

Example 57

Ac-Asn-homoArg-Thr-Nle-c[Glu-Hyp-D-Phe-Arg-Trp-Lys]-NH$_2$
LC/MS (system 3): Rt=5.91 min; ((m+2)/2)=701

Example 58

Ac-Gln-Asn-Thr-Nle-c[Glu-Hyp-D-Phe-Arg-Trp-Lys]-NH$_2$
LC/MS (system 3): Rt=7.11 min; ((m+2)/2)=680

Example 59

Ac-Asn-Asn-Thr-Nle-c[Glu-Hyp-D-Phe-Arg-Trp-Lys]-NH$_2$
LC/MS (system 3): Rt=6.95 min; ((m+2)/2)=672

Example 60

Ac-D-Ser-Tyr-Gly-Nle-c[Glu-Hyp-D-Phe-Arg-Trp-Lys]-NH$_2$
LC/MS (system 3): Rt=8.78 min; ((m+2)/2)=661

Example 61

Ac-Gln-Tyr-Gly-Nle-c[Glu-Hyp-D-Phe-Arg-Trp-Lys]-NH$_2$
LC/MS (system 3): Rt=8.48 min; ((m+2)/2)=682

Example 62

Ac-Ser-His-Gly-Nle-c[Glu-Hyp-D-Phe-Arg-Trp-Lys]-NH$_2$
LC/MS (system 3): Rt=5.73 min; ((m+2)/2)=648

Example 63

Ac-Asn-His-Gly-Nle-c[Glu-Hyp-D-Phe-Arg-Trp-Lys]-NH$_2$
LC/MS (system 3): Rt=5.56 min; ((m+2)/2)=662

Example 64

Ac-Ser-Arg-Gly-Nle-c[Glu-Hyp-D-Phe-Arg-Trp-Lys]-NH$_2$
LC/MS (system 3): Rt=5.71 min; ((m+2)/2)=658

Example 65

Ac-Asn-Arg-Gly-Nle-c[Glu-Hyp-D-Phe-Arg-Trp-Lys]-NH$_2$
LC/MS (system 3): Rt=5.77 min; ((m+2)/2)=672

Example 66

Ac-D-Ser-homoArg-Gly-Nle-c[Glu-Hyp-D-Phe-Arg-Trp-Lys]-NH$_2$
LC/MS (system 3): Rt=5.93 min; ((m+2)/2)=665

Example 67

Ac-Gln-homoArg-Gly-Nle-c[Glu-Hyp-D-Phe-Arg-Trp-Lys]-NH$_2$
LC/MS (system 3): Rt=5.72 min; ((m+2)/2)=685

Example 68

Ac-Ser-Asn-Gly-Nle-c[Glu-Hyp-D-Phe-Arg-Trp-Lys]-NH$_2$
LC/MS (system 3): Rt=6.84 min; ((m+2)/2)=637

Example 69

Ac-Ser-Tyr-Ser-Nle-c[Glu-Hyp-D-Phe-Arg-Trp-Lys]-NH$_2$
LC/MS (system 3): Rt=8.68 min; ((m+2)/2)=676

Example 70

Ac-Ser-His-Ser-Nle-c[Glu-Hyp-D-Phe-Arg-Trp-Lys]-NH$_2$
LC/MS (system 3): Rt=5.73 min; ((m+2)/2)=664

Example 71

Ac-Ser-Arg-Ser-Nle-c[Glu-Hyp-D-Phe-Arg-Trp-Lys]-NH$_2$
LC/MS (system 3): Rt=5.94 min; ((m+2)/2)=673

Example 72

Ac-Ser-His-Ser-Nle-c[Asp-Hyp-D-Phe-Arg-Trp-Lys]-NH$_2$
LC/MS (system 3): Rt=5.65 min; ((m+2)/2)=656

Example 73

Ac-Ser-His-Ser-Nle-c[Glu-Ser-D-Phe-Arg-Trp-Lys]-NH$_2$
LC/MS (system 3): Rt=5.4 min; ((m+2)/2)=650

Example 74

Ac-Ser-His-Ser-Nle-c[Glu-Hyp-D-Phe(3-trifluoromethyl)-Arg-Trp-Lys]-NH$_2$
LC/MS (system 3): Rt=7.41 min; ((m+2)/2)=697

Example 75

Ac-Ser-His-Ser-Nle-c[Glu-Hyp-D-Phe(2-methyl)-Arg-Trp-Lys]-NH$_2$
LC/MS (system 3): Rt=5.88 min; ((m+2)/2)=670

Example 76

Ac-Ser-His-Ser-Nle-c[Glu-Hyp-D-Phe(2-chloro)-Arg-Trp-Lys]-NH$_2$
LC/MS (system 3): Rt=6.22 min; ((m+2)/2)=680

Example 77

Ac-Nle-c[Asp-Thr-D-Phe-Arg-Trp-Lys]-NH$_2$
LC/MS (system 3): Rt=9.87 min; (m+1)=989

Example 78

Ac-Nle-c[Asp-Dap-D-Phe-Arg-Trp-Lys]-NH$_2$
LC/MS (system 3): Rt=9.58 min; (m+1)=974

Example 79

Ac-Nle-c[Asp-(4-thiazolyl)Ala-D-Phe-Arg-Trp-Lys]-NH$_2$
LC/MS (system 3): Rt=11.87 min; ((m+2)/2)=521

Example 80

Ac-Nle-c[Asp-Phe(4-amino)-D-Phe-Arg-Trp-Lys]-NH$_2$
LC/MS (system 3): Rt=8.98 min; ((m+2)/2)=525

Example 81

Ac-Nle-c[Asp-Cit-D-Phe-Arg-Trp-Lys]-NH$_2$
LC/MS (system 3): Rt=9.78 min; ((m+2)/2)=523

Example 82

Ac-Ser-His-Ser-Nle-c[Asp-(4-thiazolyl)Ala-D-Phe-Arg-Trp-Lys]-NH$_2$
LC/MS (system 3): Rt=8.28 min; ((m+2)/2)=677

Pharmacological Methods

Assay (I) Experimental Protocol for Efficacy Testing on Appetite with MC4 Analogues, Using a ad Libitum Fed Rat Model.

TAC:SPRD @mol rats or Wistar rats from M&B Breeding and Research Centre A/S, Denmark are used for the experiments. The rats have a bodyweight 200-250 g at the start of experiment. The rats arrive at least 10-14 days before start of experiment with a bodyweight of 180-200 g. Each dose of compound is tested in a group of 8 rats. A vehicle group of 8 rats is included in each set of testing.

When the animals arrive they are housed individually in a reversed light/dark phase (lights off 7:30 am, lights on 7:30 pm), meaning that lights are off during daytime and on during nighttime. Since rats normally initiate food intake when light go off and eat the major part of their daily food intake during night, this set up means that we have reversed the initiation time of food intake till 7:30, when lights go off. During the habituating period of 10-14 days, the rats have free access to food and water, In this period the animals are handled at least 3 times. The experiment is conducted in the rats' home cages. Immediately before dosing the rats are randomised to the different treatment groups (n=8) by bodyweight. They are dosed according to bodyweight at between 7:00 am, with a 1-3 mg/kg solution either, ip, po or sc. The dosing time is recorded for each group. Following dosing the rats are returned to their home cages, where they now have access to food and water. The food consumption is recorded individually, each hour for 7 hours, and then after 24 h and sometimes 48 h. At the end of the experimental session, the animals are euthanised.

The individual data are recorded in Microsoft excel sheets. Outliers are excluded after using the Grubbs statistical evaluation test for outliers and the result presented graphically by using the GraphPad Prism program.

Assay (II) Melanocortin Receptor 3 and 5 (MC3 and MC5) cAMP Functional Assay Using the AlphaScreen™ cAMP Detection Kit The cAMP assays for MC3 and MC5 receptors are performed on cells stably expressing the MC3 and MC5 receptors respectively. The receptors were cloned from cDNA by PCR and inserted into the pcDNA 3 expression vector. Stable clones were selected using 1 mg/ml G418.

Cells at app. 80-90% confluence are washed 3× with PBS, lifted from the plates with Versene and diluted in PBS. Centrifuged 2 min at 1300 rpm, and the supernatant removed. The cells are washed twice with stimulation buffer, and resuspended in stimulation buffer to a final concentration of 1 or $2 \times 10^6$ cells/ml. 25 µl cell suspension is added to the microtiter plates containing 25 µl of test-compound or reference compound (all diluted in stimulation buffer). The plates are incubated for 30 minutes at room temperature (RT) on a plateshaker that shakes at low rate. The reaction is stopped by adding and 25 µl acceptor beads with anti-cAMP and 2 min later 50 µl donor beads per well with biotinylated cAMP in a lysis buffer. The plates are then sealed with plastic, shaken for 30 minutes, and allowed to stand overnight, and counted in the Alpha™ microplate reader.

$EC_{50}$ values are calculated by non-linear regression analysis of dose response curves (6 points minimum) using the windows program GraphPad Prism, GraphPad software, USA. All results are expressed in nM.

For measuring antagonistic activity in the MC3 functional cAMP assay the MC3 receptors are stimulated with 3 nM ☐-MSH, and inhibited by increasing amount of potential antagonist. The $IC_{50}$ value of the antagonist is defined at the concentration that inhibits MC3 stimulation by 50%.

Assay (III) Melanocortin Receptor 4 (MC4) cAMP Assay

BHK cells expressing the MC4 receptor are stimulated with potential MC4 agonists, and the degree of stimulation of cAMP is measured using the Flash Plate® cAMP assay (NEN™ Life Science Products cat no SMP004).

The MC4 receptor expressing BHK cells were made by transfecting the cDNA encoding MC4 receptor into BHK570/KZ10-20-48, and selecting for stable clones expressing the MC4 receptor. The MC4 receptor cDNA was bought from Euroscreen in addition to a CHO cell line expressing the MC4 receptor. The cells are grown in DMEM, 10% FCS, 1 mg/ml G418, 250 nM MTX and 1% penicillin/streptomycin.

Cells at app. 80-90% confluence are washed 3× with PBS, lifted from the plates with Versene and diluted in PBS. Centrifuged 2 min at 1300 rpm, and the supernatant removed. The cells are washed twice with stimulation buffer, and resuspended in stimulation buffer to a final concentration of 0.75× $10^6$ cells/ml. (Use 7 ml/96 well plate). 50 µl cell suspension is added to the Flashplate containing 50 µl of test-compound or reference compound (all diluted in $H_2O$). The mixture is shaken for 5 minutes, and allowed to stand for 25 minutes at RT. The reaction is stopped with 100 µl Detection Mix pro well (Detection Mix=1 1 ml Detection Buffer+100 µl (~2 µCi) cAMP [$^{125}I$] Tracer). The plates are then sealed with plastic, shaken for 30 minutes, and allowed to stand overnight (or for 2 hours), and counted in the Topcounter 2 min/well. In general the assay procedure described in the flash plate kit-protocol (Flash Plate® cAMP assay (NEN™ Life Science Products cat no SMP004)). However the cAMP standards are diluted in 0.1% HSA and 0.0050% tween 20 and not in stimulation buffer.

$EC_{50}$ values is calculated by non-linear regression analysis of dose response curves (6 points minimum) using the windows program GraphPad Prism, GraphPad software, USA. All results are expressed in nM.

Assay (IV) Melanocortin Receptor 1 (MC1) Binding Assay

The MC1 receptor binding assay is performed on HEK293 cell membranes stably expressing the MC1 receptor. The assay is performed in a total volume of 250 µl; 25 µl $^{125}$NDP-α-MSH (22 pM in final concentration) 25 µl test compound/control and 200 µl cell membrane (35 µg/ml). Test-compounds are dissolved in DMSO. Radioligand, membranes and test-compounds are diluted in buffer; 25 mM HEPES pH 7.4, 0.1 mM $CaCl_2$, 1 mM $MgSO_4$, 1 mM EDTA, 0.1% HSA and 0.005% Tween-20. The samples are incubated at 30° C. for 90 min in the Greiner microtitter plates and separated with GF/B filters that are pre-wetted for 60 min in 0.5% PEI, and washed 2-3 times with NaCl (0.90%) before separation of bound from unbound radio ligand by filtration. After filtration the filters are washed with ice-cold 0.9% NaCl 10 times. The filters are dried at 50° C. for 30 min, sealed and 30 pl Microscint 0 (Packard, cat no. 6013616) are added to each well and the plates are counted in a Topcounter 1 min/well.

The data are analysed by a non-linear regression analysis of binding curves, using a windows program GraphPad Prism, GraphPad software, USA.

Assay (V) Melanocortin Receptor 4 (MC4) Binding Assay

In vitro $^{125}$NDP-α-MSH Binding to Recombinant BHK Cells Expressing Human MC4 receptor (Filtration Assay).

The assay is performed in 5 ml minisorb vials, (Sarstedt No. 55.526) or in 96 well filterplate, Millipore MADVN 6550 and using BHK cells expressing the human MC4 receptor (obtained from Professer Wikberg, Uppsala, Sweden). The BHK cells are kept at −80° C until assay, and the assays is run directly on a dilution of this cell suspension, without further preparation. The suspension is diluted to give maximal 10% specific binding, app 50-100 fold dilution. The assay is performed in a total volume of 200 µl; 50 µl cell suspension, 50 µl $^{125}$NDP-α-MSH (~79 pM in final concentration), 50 µl test-peptide and 50 µl binding buffer pH 7 is mixed and incubated for 2 h at 25° C. (Binding buffer; 25 mM HEPES pH 7.0, 1 mM $CaC_2$, 1 mM $MgSO_4$, 1 mM EGTA, 0.02% Bacitracin and 0.2% BSA). Peptides are dissolved in $H_2O$ and diluted in binding buffer. Radioligand and membranes are diluted in binding buffer. The incubation is stopped by dilution with 5 ml ice-cold 0.9% NaCl, followed by rapid filtration through Whatman GF/C filters pre-treated for 1 hour with 0.5% polyethyleneimine. The filters are washed with 3×5 ml ice-cold NaCl. The radioactivity retained on the filters is counted using a Cobra II auto gamma counter.

The data are analysed by a non-linear regression analysis of binding curves, using a windows program GraphPad Prism, GraphPad software, USA.

Assay (VI) Evaluation of Energy Expenditure

TAC:SPRD rats or Wistar rats from M&B Breeding and Research Centre A/S, Denmark are used. After at least one week of acclimatization, rats are placed individually to the metabolic chambers (Oxymax system, Columbus Instruments, Columbus, Ohio; systems calibrated daily). During the measurement, animals have free access to water, but no food is provided to the chambers. Light:dark cycle is 12:12, lights on at 6.00. After the animals have spent in the chambers ca 2 hours (i.e. when the baseline energy expenditure is reached), compound or vehicle are administrated (po, ip or sc), and recording is continued in order to establish the action time of the compound. Data for each animal (oxygen consumption, carbon dioxide production and flow rate) are collected every 10-18 min for totally 22 hours: 2 hours of adaptation (baseline) and 20 hours of measurement. Correction for the changes in $O_2$ and $CO_2$ content in the flow-in air is done in each 10-18 min cycle.

Data are calculated per metabolic weight ((kg body weight)$^{0.75}$) for oxygen consumption and carbon dioxide production, and per animal for heat. Oxygen consumption ($VO_2$) is regarded as the major energy expenditure parameter of interest.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

The invention claimed is:

1. A peptide according to formula I:

X1-X2-X3-X4-X5-X6-X7-R$^1$   (I)

wherein,

X1 represents Nle or X-Nle, wherein X represents an amino acid or a di-, tri-, tetra- or penta-peptide consisting of polar or hydrophilic amino acid residues selected from the D and L forms of Asp, Glu, His, Arg, homoArg, Tyr, Asn, Ser, Thr, Lys, Orn, Dap, Dab and Gln and wherein X may furthermore contain one or two amino acid residues selected from Gly, β-Ala or the D and L forms of Pro, Hyp, and Ala;

and wherein the N-terminal amino group of X1 may optionally be acylated with an acyl moiety, R—C(O)—, wherein R presents an alkyl or alkenyl with up to 6 carbon atoms, wherein said alkyl may optionally be substituted with one or more substituents selected from hydroxyl and amino;

X2 represents Glu or Asp;

X3 represents Cit, Dab, Dap, cyclohexylglycine, cyclohexylalanine, Val, Ile, tert-butylglycine, Leu, Tyr, Glu, Ala, Nle, Met, Met(O), Met(O$_2$), Gln, Gln(alkyl), Gln(aryl), Asn, Asn(alkyl), Asn(aryl), Ser, Thr, Cys, Pro, Hyp, Tic, 2-PyAla, 3-PyAla, 4-PyAla, (2-thienyl)alanine, 3-(thienyl)alanine, (4-thiazolyl)Ala, (2-furyl)alanine, (3-furyl)alanine, Phe, wherein the phenyl moiety of said Phe is optionally substituted by halogen, hydroxyl, alkoxy, nitro, benzoyl, methyl, trifluoromethyl, amino, or cyano;

X4 represents D-Phe, wherein the phenyl moiety in D-Phe may optionally be substituted with one or more substituents selected from halogen, hydroxy, alkoxy, nitro, methyl, trifluoromethyl and cyano;

X5 represents Arg;

X6 represents Trp;

X7 represents Lys or Orn, wherein to make the peptide of formula I cyclic an amide bond is formed between the side chain carboxyl of X2 and the side chain amine group of X7;

R1 represents —N(R")₂ or —OR" with each R" independently representing hydrogen or $C_{1-6}$alkyl, which may optionally be substituted with one or more amine or hydroxyl;

provided that if X3 represents Hyp, Ala, Pro, Glu, Lys or Gln, and X1 represents Ac-Nle, then X2 does not represent Asp; or a pharmaceutically acceptable salt thereof.

2. A peptide according to claim 1, wherein R represents —N(R")₂, wherein each R" represents hydrogen, or wherein one R" represents $C_{1-3}$alkyl optionally substituted with one or more substituents selected from hydroxyl and amino.

3. The peptide according to claim 1, wherein X1 represents Nle or R—C(O)-Nle.

4. The peptide according to claim 1, wherein X represents Z1-Z2-Z3-Z4-Z5, Z2-Z3-Z4-Z5, Z3-Z4-Z5, Z4-Z5 or Z5, wherein Z1 represents an amino acid; Z2 represents an amino acid;

Z3 represents Ser, Ala, Lys, Gln, Asn or D-Ser;
Z4 represents Tyr, Lys, His, Arg, homoArg, Gln or Asn; and
Z5 represents Ser, Dab, Ala, Hyp, Gly, Pro or Thr;
and wherein the N-terminus of X is acylated with R—C(O)—.

5. The peptide according to claim 4, wherein X represents
Ala-Lys-Tyr-Ser- (SEQ ID NO: 1),
Ala-Lys-Ala-,
Asn-Arg-Gly-,
Asn-Arg-Hyp-,
Asn-Asn-Pro-,
Asn-Asn-Thr-,
Asn-His-Gly-,
Asn-His-Pro-,
Asn-homoArg-Hyp-,
Asn-homoArg-Thr-,
Asn-Tyr-Ser-,
Dab-,
D-Ser-Arg-Pro-,
D-Ser-Arg-Thr-,
D-Ser-Asn-Hyp-,
D-Ser-Asn-Ser-,
D-Ser-His-Ser-,
D-Ser-His-Thr-,
D-Ser-homoArg-Gly-,
D-Ser-homoArg-Pro-,
D-Ser-Tyr-Gly-,
D-Ser-Tyr-Hyp-,
Gln-Arg-Hyp-,
Gln-Arg-Ser-,
Gln-Asn-Pro-,
Gln-Asn-Thr-,
Gln-His-Hyp-,
Gln-His-Thr-,
Gln-homoArg-Gly-,
Gln-homoArg-Ser-,
Gln-Tyr-Gly-,
Gln-Tyr-Pro-,
Gly-Ser-Gln-His-Ser- (SEQ ID NO: 2),
Gly-Ser-Gln-homoArg-Ser- (SEQ ID NO: 3),
Ser-Arg-Gly-,
Ser-Arg-Pro-,
Ser-Arg-Ser-,
Ser-Arg-Thr-,
Ser-Asn-Gly-,
Ser-Asn-Ser
Ser-Gln-His-Ser- (SEQ ID NO: 4),
Ser-Gln-Ser-,
Ser-His-Gly-,
Ser-His-Hyp-,
Ser-His-Pro-,
Set-His-Set-,
Ser-homoArg-Pro-,
Ser-homoArg-Ser-,
Ser-homoArg-Thr-,
Ser-,
Ser-Tyr-Hyp-,
Ser-Tyr-Ser- or
Ser-Tyr-Thr-, each of which is acylated at the N-terminus with R—C(O)—.

6. The peptide according to claim 1, wherein R represents alkyl with up to six carbon atoms, optionally substituted with one or more substituents selected from hydroxyl and amino.

7. The peptide according to claim 6, wherein R represents methyl, ethyl, propyl, butyl, pentyl and hexyl, optionally substituted with one or more substituents selected from hydroxyl and amino.

8. The peptide according to claim 6, wherein R represents 2-hydroxy-3-methylbutanoyl or 2,4-diaminobutanoyl.

9. The peptide according to claim 5, wherein R represents alkyl with up to six carbon atoms, optionally substituted with one or more substituents selected from hydroxyl and amino.

10. The peptide according to claim 9, wherein R represents 2-hydroxy-3- methylbutanoyl or 2,4-diaminobutanoyl.

11. The peptide according to claim 1, wherein X1 represents Ac-Nle.

12. The peptide according to claim 1, wherein X1 represents Ac-Gly-Ser-Gln-His-Ser-Nle (SEQ ID NO: 5) or Ac-Ser-His-Ser-Nle (SEQ ID NO: 6).

13. The peptide according to claim 1, wherein X3 represents Met(O₂), Tic, 3-PyAla, Ser, Cit, Leu, Phe(4-amino), Phe(3,4-dichloro), Phe(3,4-difluoro), Dab, Cgl, Val, Cha, Phe, Dap, Ile, Thr, tBuGly, (4-thiazolyl)Ala, Hyp, Asn, or Gln.

14. The peptide according to claim 1, wherein X3 represents Met(O₂), Tic, 3-PyAla, Ser, Cit, Leu, Phe(4-amino), Phe(3,4-difluoro), Dab, Phe, Dap, Thr, (4-thiazolyl)Ala, or Hyp.

15. The peptide according to claim 1, wherein X3 represents Tic, Met(O₂), Ser, Hyp, Cit, Dap, (4-thiazolyl)Ala or 3-PyAla.

16. The peptide according to claim 1, wherein X4 represents D-Phe, D-Phe(4-chloro), D-Phe(4-iodo), D-Phe(3-trifluoromethyl), D-Phe(2-methyl) or D-Phe(2-chloro).

17. The peptide according to claim 1, wherein X2 represents Glu and X7 represents Lys.

18. The peptide according to claim 1, wherein X2 represents Asp and X7 represents Lys.

19. The peptide according to claim 1, wherein X2-X3-X4-X5-X6-X7 represents c[X2-X3-D-Phe-Arg-Trp-Lys], wherein X2 represents Glu or Asp;
X3 represents Met(O₂), Tic, 3-PyAla, Ser, Cit, Leu, Phe(4-amino), Phe(3,4-dichloro), Phe(3,4-difluoro), Dab, Cgl, Val, Cha, Phe, Dap, Ile, Thr, tBuGly, (4-thiazolyl)Ala or Hyp.

20. The peptide according to claim 19, wherein X2 represents Glu, and X3 represents Tic, Met(O₂), Ser, Hyp, Cit, Dap, (4-thiazolyl)Ala or 3-PyAla.

21. The peptide according to claim 20, wherein X3 represents Hyp.

22. The peptide according to claim 19, wherein X2-X3-X4-X5-X6-X7 represents c[Glu-Hyp-D-Phe-Arg-Trp-Lys].

23. The peptide according to claim 1,
wherein
X3 represents Tic, Met(O₂), Ser, Hyp, Cit, Dap, (4-thiazolyl)Ala or 3-PyAla, and X1 represents Ac-Gly-Ser-Gln-His-Ser-Nle-(SEQ ID NO: 5) or Ac-Nle.

24. The peptide according to claim 1, wherein X3 represents Tic, Met($O_2$), Ser, Hyp, Cit, Dap, (4-thiazolyl)Ala or 3-PyAla;
X1 represents Ac-Gly-Ser-Gln-His-Ser-Nle-(SEQ ID NO: 5) or Ac-Nle;
X4 represents D-Phe; and
X6 represents Trp; and
X2 represents Asp.

25. The peptide according to claim 1,
wherein
X3 represents Tic, Met($O_2$), Ser, Hyp, Cit, Dap, (4-thiazolyl)Ala or 3-PyAla;
X1 represents Ac-Gly-Ser-Gln-His-Ser-Nle-(SEQ ID NO: 5) or Ac-Nle;
X4 represents D-Phe;
X6 represents Trp; and
X2 represents Glu.

26. A peptide is selected from:
Ac-Nle-c[Glu-3-PyAla-D-Phe-Arg-Trp-Lys]-NH$_2$ (SEQ ID NO: 6)
Ac-Nle-c[Glu-Leu-D-Phe-Arg-Trp-Lys]-NH$_2$ (SEQ ID NO: 7)
Ac-Nle-c[Glu-Phe(3,4-dichloro)-D-Phe-Arg-Trp-Lys]-NH$_2$ (SEQ ID NO: 8)
Ac-Nle-c[Glu-Met($O_2$)-D-Phe-Arg-Trp-Lys]-NH$_2$ (SEQ ID NO: 9)
Ac-Nle-c[Glu-Dab-D-Phe-Arg-Trp-Lys]-NH$_2$ (SEQ ID NO: 10)
Ac-Nle-c[Glu-CgI-D-Phe-Arg-Trp-Lys]-NH$_2$ (SEQ ID NO: 11)
Ac-Nle-c[Glu-Val-D-Phe-Arg-Trp-Lys]-NH$_2$ (SEQ ID NO: 12)
Ac-Nle-c[Glu-Tic-D-Phe-Arg-Trp-Lys]-NH$_2$ (SEQ ID NO: 13)
Ac-Nle-c[Glu-Cha-D-Phe-Arg-Trp-Lys]-NH$_2$ (SEQ ID NO: 14)
Ac-Nle-c[Glu-Ile-D-Phe-Arg-Trp-Lys]-NH$_2$ (SEQ ID NO: 15)
Ac-Nle-c[Glu-tBuGly-D-Phe-Arg-Trp-Lys]-NH$_2$ (SEQ ID NO: 16)
Ac-Nle-c[Glu-Phe(3,4-difluoro)-D-Phe-Arg-Trp-Lys]-NH$_2$ (SEQ ID NO: 17)
Ac-Nle-c[Glu-Phe-D-Phe-Arg-Trp-Lys]-NH$_2$ (SEQ ID NO: 18)
Ac-Ser-Tyr-Ser-Nle-c[Glu-3-PyAla-D-Phe-Arg-Trp-Lys]-NH$_2$ (SEQ ID NO: 19)
H-Ala-Lys-Tyr-Ser-Nle-c[Glu-3-PyAla-D-Phe-Arg-Trp-Lys]-NH$_2$ (SEQ ID NO: 20)
2-Hydroxy-3-methylbutanoyl-Ser-Nle-c[Glu-3-PyAla-D-Phe-Arg-Trp-Lys]-NH$_2$(SEQ ID NO: 21)
H-Dab-Nle-c[Glu-3-PyAla-D-Phe-Arg-Trp-Lys]-NH$_2$ (SEQ ID NO: 22)
H-Ala-Lys-Ala-Nle-c[Glu-Hyp-D-Phe-Arg-Trp-Lys]-NH$_2$ (SEQ ID NO: 23)
Ac-Nle-c[Glu-Hyp-D-Phe(4-iodo)-Arg-Trp-Lys]-NH$_2$ (SEQ ID NO: 24)
Hex-5-enoyl-Nle-c[Glu-Hyp-D-Phe-Arg-Trp-Lys]-NH$_2$ (SEQ ID NO: 25)
Ac-Gly-Ser-Gln-His-Ser-Nle-c[Glu-Hyp-D-Phe-Arg-Trp-Lys]-NH$_2$ (SEQ ID NO: 26)
Ac-Gly-Ser-Gln-homoArg-Ser-Nle-c[Glu-Hyp-D-Phe-Arg-Trp-Lys]-NH$_2$ (SEQ ID NO: 27)
Ac-Gly-Ser-Gln-His-Ser-Nle-c[Glu-Met($O_{o2}$)-D-Phe-Arg-Trp-Lys]-NH$_2$ (SEQ ID NO :28)
Ac-Nle-c[Glu-Hyp-D-Phe-Arg-Trp-Lys]-NH$_2$ (SEQ ID NO: 29)
Ac-Nle-c[Glu-Hyp-D-Phe-Arg-Trp-Lys]-(2-aminoethyl)amide (SEQ ID NO: 30)
Ac-Nle-c[Asp-Phe(4-amino)-D-Phe(4-chloro)-Arg-Trp-Lys]-NH$_2$ (SEQ ID NO: 31)
Ac-Asn-Tyr-Ser-Nle-c[Glu-Hyp-D-Phe-Arg-Trp-Lys]-NH$_2$ (SEQ ID NO: 32)
Ac-D-Ser-His-Ser-Nle-c[Glu-Hyp-D-Phe-Arg-Trp-Lys]-NH$_2$ (SEQ ID NO: 33)
Ac-Gln-Arg-Ser-Nle-c[Glu-Hyp-D-Phe-Arg-Trp-Lys]-NH$_2$ (SEQ ID NO: 34)
Ac-Ser-homoArg-Ser-Nle-c[Glu-Hyp-D-Phe-Arg-Trp-Lys]-NH$_2$ (SEQ ID NO: 35)
Ac-Gln-homoArg-Ser-Nle-c[Glu-Hyp-D-Phe-Arg-Trp-Lys]-NH$_2$ (SEQ ID NO: 36)
Ac-Ser-Asn-Ser-Nle-c[Glu-Hyp-D-Phe-Arg-Trp-Lys]-NH$_2$ (SEQ ID NO: 37)
Ac-D-Ser-Asn-Ser-Nle-c[Glu-Hyp-D-Phe-Arg-Trp-Lys]-NH$_2$ (SEQ ID NO: 38)
Ac-Ser-Tyr-Hyp-Nle-c[Glu-Hyp-D-Phe-Arg-Trp-Lys]-NH$_2$ (SEQ ID NO: 39)
Ac-D-Ser-Tyr-Hyp-Nle-c[Glu-Hyp-D-Phe-Arg-Trp-Lys]-NH$_2$ (SEQ ID NO: 40)
Ac-Ser-His-Hyp-Nle-c[Glu-Hyp-D-Phe-Arg-Trp-Lys]-NH$_2$ (SEQ ID NO: 41)
Ac-Gln-His-Hyp-Nle-c[Glu-Hyp-D-Phe-Arg-Trp-Lys]-NH$_2$ (SEQ ID NO: 42)
Ac-Gln-Arg-Hyp-Nle-c[Glu-Hyp-D-Phe-Arg-Trp-Lys]-NH$_2$ (SEQ ID NO: 43)
Ac-Asn-Arg-Hyp-Nle-c[Glu-Hyp-D-Phe-Arg-Trp-Lys]-NH$_2$ (SEQ ID NO: 44)
Ac-Asn-homoArg-Hyp-Nle-c[Glu-Hyp-D-Phe-Arg-Trp-Lys]-NH$_2$ (SEQ ID NO: 45)
Ac-D-Ser-Asn-Hyp-Nle-c[Glu-Hyp-D-Phe-Arg-Trp-Lys]-NH$_2$ (SEQ ID NO: 46)
Ac-Gln-Tyr-Pro-Nle-c[Glu-Hyp-D-Phe-Arg-Trp-Lys]-NH$_2$ (SEQ ID NO: 47)
Ac-Ser-His-Pro-Nle-c[Glu-Hyp-D-Phe-Arg-Trp-Lys]-NH$_2$ (SEQ ID NO: 48)
Ac-Asn-His-Pro-Nle-c[Glu-Hyp-D-Phe-Arg-Trp-Lys]-NH$_2$ (SEQ ID NO: 49)
Ac-Ser-Arg-Pro-Nle-c[Glu-Hyp-D-Phe-Arg-Trp-Lys]-NH$_2$ (SEQ ID NO: 50)
Ac-D-Ser-Arg-Pro-Nle-c[Glu-Hyp-D-Phe-Arg-Trp-Lys]-NH$_2$ (SEQ ID NO: 51)
Ac-Ser-homoArg-Pro-Nle-c[Glu-Hyp-D-Phe-Arg-Trp-Lys]-NH$_2$ (SEQ ID NO: 52)
Ac-D-Ser-homoArg-Pro-Nle-c[Glu-Hyp-D-Phe-Arg-Trp-Lys]-NH$_2$ (SEQ ID NO: 53)
Ac-Gln-Asn-Pro-Nle-c[Glu-Hyp-D-Phe-Arg-Trp-Lys]-NH$_2$ (SEQ ID NO: 54)
Ac-Asn-Asn-Pro-Nle-c[Glu-Hyp-D-Phe-Arg-Trp-Lys]-NH$_2$ (SEQ ID NO: 55)
Ac-Ser-Tyr-Thr-Nle-c[Glu-Hyp-D-Phe-Arg-Trp-Lys]-NH$_2$ (SEQ ID NO: 56)
Ac-D-Ser-His-Thr-Nle-c[Glu-Hyp-D-Phe-Arg-Trp-Lys]-NH$_2$ (SEQ ID NO: 57)
Ac-Gln-His-Thr-Nle-c[Glu-Hyp-D-Phe-Arg-Trp-Lys]-NH$_2$ (SEQ ID NO: 58)
Ac-Ser-Arg-Thr-Nle-c[Glu-Hyp-D-Phe-Arg-Trp-Lys]-NH$_2$ (SEQ ID NO: 59)
Ac-D-Ser-Arg-Thr-Nle-c[Glu-Hyp-D-Phe-Arg-Trp-Lys]-NH$_2$ (SEQ ID NO: 60)
Ac-Ser-homoArg-Thr-Nle-c[Glu-Hyp-D-Phe-Arg-Trp-Lys]-NH$_2$ (SEQ ID NO: 61)

Ac-Asn-homoArg-Thr-Nle-c[Glu-Hyp-D-Phe-Arg-Trp-Lys]-NH$_2$ (SEQ ID NO: 62)
Ac-Gln-Asn-Thr-Nle-c[Glu-Hyp-D-Phe-Arg-Trp-Lys]-NH$_2$ (SEQ ID NO: 63)
Ac-Asn-Asn-Thr-Nle-c[Glu-Hyp-D-Phe-Arg-Trp-Lys]-NH$_2$ (SEQ ID NO: 64)
Ac-D-Ser-Tyr-Gly-Nle-c[Glu-Hyp-D-Phe-Arg-Trp-Lys]-NH$_2$ (SEQ ID NO: 65)
Ac-Gln-Tyr-Gly-Nle-c[Glu-Hyp-D-Phe-Arg-Trp-Lys]-NH$_2$ (SEQ ID NO: 66)
Ac-Ser-His-Gly-Nle-c[Glu-Hyp-D-Phe-Arg-Trp-Lys]-NH$_2$ (SEQ ID NO: 67)
Ac-Asn-His-Gly-Nle-c[Glu-Hyp-D-Phe-Arg-Trp-Lys]-NH$_2$ (SEQ ID NO: 68)
Ac-Ser-Arg-Gly-Nle-c[Glu-Hyp-D-Phe-Arg-Trp-Lys]-NH$_2$ (SEQ ID NO: 69)
Ac-Asn-Arg-Gly-Nle-c[Glu-Hyp-D-Phe-Arg-Trp-Lys]-NH$_2$ (SEQ ID NO: 70)
Ac-D-Ser-homoArg-Gly-Nle-c[Glu-Hyp-D-Phe-Arg-Trp-Lys]-NH$_2$ (SEQ ID NO: 71)
Ac-Gln-homoArg-Gly-Nle-c[Glu-Hyp-D-Phe-Arg-Trp-Lys]-NH$_2$ (SEQ ID NO: 72)
Ac-Ser-Asn-Gly-Nle-c[Glu-Hyp-D-Phe-Arg-Trp-Lys]-NH$_2$ (SEQ ID NO: 73)
Ac-Ser-Tyr-Ser-Nle-c[Glu-Hyp-D-Phe-Arg-Trp-Lys]-NH$_2$ (SEQ ID NO: 74)
Ac-Ser-His-Ser-Nle-c[Glu-Hyp-D-Phe-Arg-Trp-Lys]-NH$_2$ (SEQ ID NO: 75)
Ac-Ser-Arg-Ser-Nle-c[Glu-Hyp-D-Phe-Arg-Trp-Lys]-NH$_2$ (SEQ ID NO: 76)
Ac-Ser-His-Ser-Nle-c[Asp-Hyp-D-Phe-Arg-Trp-Lys]-NH$_2$ (SEQ ID NO: 77)
Ac-Ser-His-Ser-Nle-c[Glu-Ser-D-Phe-Arg-Trp-Lys]-NH$_2$ (SEQ ID NO: 78)
Ac-Ser-His-Ser-Nle-c[Glu-Hyp-D-Phe(3-trifluoromethyl)-Arg-Trp-Lys]-NH$_2$ (SEQ ID NO: 79)
Ac-Ser-His-Ser-Nle-c[Glu-Hyp-D-Phe(2-methyl)-Arg-Trp-Lys]-NH$_2$ (SEQ ID NO: 80)
Ac-Ser-His-Ser-Nle-c[Glu-Hyp-D-Phe(2-chloro)-Arg-Trp-Lys]-NH$_2$ (SEQ ID NO :81)
Ac-Nle-c[Asp-Thr-D-Phe-Arg-Trp-Lys]-NH$_2$ (SEQ ID NO: 82)
Ac-Nle-c[Asp-Dap-D-Phe-Arg-Trp-Lys]-NH$_2$ (SEQ ID NO: 83)
Ac-Nle-c[Asp-(4-thiazolyl)Ala-D-Phe-Arg-Trp-Lys]-NH$_2$ (SEQ ID NO: 84)
Ac-Nle-c[Asp-Phe(4-amino)-D-Phe-Arg-Trp-Lys]-NH$_2$ (SEQ ID NO: 85)
Ac-Nle-c[Asp-Cit-D-Phe-Arg-Trp-Lys]-NH$_2$ (SEQ ID NO: 86) and
Ac-Ser-His-Ser-Nle-c[Asp-(4-thiazolyl)Ala-D-Phe-Arg-Trp-Lys]-NH$_2$ (SEQ ID NO: 87).

27. A pharmaceutically acceptable composition comprising a therapeutically effective amount of a peptide according to claim 1.

28. A pharmaceutical composition comprising a peptide according to claim 23.

29. A pharmaceutical composition comprising a peptide according to claim 24.

30. A pharmaceutical composition comprising a peptide according to claim 25.

31. A pharmaceutical composition comprising a peptide according to claim 26.

* * * * *

```
                         SEQUENCE LISTING

<160> NUMBER OF SEQ ID NOS: 87

<210> SEQ ID NO 1
<211> LENGTH: 4
<212> TYPE: PRT
<213> ORGANISM: Artificial
<220> FEATURE:
<223> OTHER INFORMATION: MT-II analogue

<400> SEQUENCE: 1

Ala Lys Tyr Ser
1

<210> SEQ ID NO 2
<211> LENGTH: 5
<212> TYPE: PRT
<213> ORGANISM: Artificial
<220> FEATURE:
<223> OTHER INFORMATION: MT-II analogue

<400> SEQUENCE: 2

Gly Ser Gln His Ser
1               5

<210> SEQ ID NO 3
<211> LENGTH: 5
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (4)..(4)
<223> OTHER INFORMATION: Homo-Arg

<400> SEQUENCE: 3

Gly Ser Gln Xaa Ser
1               5

<210> SEQ ID NO 4
<211> LENGTH: 4
<212> TYPE: PRT
<213> ORGANISM: Artificial
<220> FEATURE:
<223> OTHER INFORMATION: MT-II analogue
```

```
<400> SEQUENCE: 4

Ser Gln His Ser
1

<210> SEQ ID NO 5
<211> LENGTH: 6
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: Nle

<400> SEQUENCE: 5

Gly Ser Gln His Ser Xaa
1               5

<210> SEQ ID NO 6
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 3-PyAla
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (6)..(6)
<223> OTHER INFORMATION: AMIDATION

<400> SEQUENCE: 6

Xaa Glu Xaa Phe Arg Trp Lys
1               5

<210> SEQ ID NO 7
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (4)..(4)
<223> OTHER INFORMATION: d form
<220> FEATURE:
<221> NAME/KEY: MOD_RES
<222> LOCATION: (7)..(7)
<223> OTHER INFORMATION: AMIDATION

<400> SEQUENCE: 7

Xaa Glu Leu Phe Arg Trp Lys
1               5

<210> SEQ ID NO 8
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 3,4-dichloro
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 8

Xaa Glu Phe Phe Arg Trp Lys
1               5

<210> SEQ ID NO 9
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: Met(O2)
<220> FEATURE:
```

```
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 9

Xaa Gln Met Phe Arg Trp Lys
1               5

<210> SEQ ID NO 10
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: Dbu
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 10

Xaa Glu Xaa Phe Arg Trp Lys
1               5

<210> SEQ ID NO 11
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(6)
<223> OTHER INFORMATION: Bridge
<220> FEATURE:
<221> NAME/KEY: MOD_RES
<222> LOCATION: (3)..(3)
<223> OTHER INFORMATION: Cyclohexyl glycine
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
```

```
<222> LOCATION: (7)..(7)
<223> OTHER INFORMATION: AMIDATION

<400> SEQUENCE: 11

Xaa Glu Xaa Phe Arg Trp Lys
1               5

<210> SEQ ID NO 12
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 12

Xaa Glu Val Phe Arg Trp Lys
1               5

<210> SEQ ID NO 13
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 1,2,3,4-tetrahydro-isoquinoline-3-carboxylic
      acid
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 13

Xaa Glu Xaa Phe Arg Trp Lys
1               5
```

```
<210> SEQ ID NO 14
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: Cyclohexyl alanine
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 14

Xaa Glu Xaa Phe Arg Trp Lys
1               5

<210> SEQ ID NO 15
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 15

Xaa Glu Ile Phe Arg Trp Lys
1               5

<210> SEQ ID NO 16
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
```

```
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: Tert Butylglycine
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 16

Xaa Glu Xaa Phe Arg Trp Lys
1               5

<210> SEQ ID NO 17
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 3,4-difluoro
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 17

Xaa Glu Phe Phe Arg Trp Lys
1               5

<210> SEQ ID NO 18
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
```

```
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 18

Xaa Glu Phe Phe Arg Trp Lys
1               5

<210> SEQ ID NO 19
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 3-PyAla
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 19

Ser Tyr Ser Xaa Glu Xaa Phe Arg Trp Lys
1               5                   10

<210> SEQ ID NO 20
<211> LENGTH: 11
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (5)..(5)
<223> OTHER INFORMATION: Nle
<220> FEATURE:
<221> NAME/KEY: MOD_RES
<222> LOCATION: (6)..(11)
<223> OTHER INFORMATION: Bridge
<220> FEATURE:
<221> NAME/KEY: MOD_RES
<222> LOCATION: (7)..(7)
<223> OTHER INFORMATION: 3-PyAla
<220> FEATURE:
<221> NAME/KEY: MOD_RES
<222> LOCATION: (8)..(8)
<223> OTHER INFORMATION: D form
```

```
<220> FEATURE:
<221> NAME/KEY: MOD_RES
<222> LOCATION: (11)..(11)
<223> OTHER INFORMATION: AMIDATION

<400> SEQUENCE: 20

Ala Lys Tyr Ser Xaa Glu Xaa Phe Arg Trp Lys
1               5                   10

<210> SEQ ID NO 21
<211> LENGTH: 8
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: 2-hydroxy-3-methyl-butanoyl-Ser
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(8)
<223> OTHER INFORMATION: Bridge
<220> FEATURE:
<221> NAME/KEY: MOD_RES
<222> LOCATION: (4)..(4)
<223> OTHER INFORMATION: 3-PyAla
<220> FEATURE:
<221> NAME/KEY: MOD_RES
<222> LOCATION: (5)..(5)
<223> OTHER INFORMATION: D form
<220> FEATURE:
<221> NAME/KEY: MOD_RES
<222> LOCATION: (8)..(8)
<223> OTHER INFORMATION: AMIDATION

<400> SEQUENCE: 21

Ser Xaa Glu Xaa Phe Arg Trp Lys
1               5

<210> SEQ ID NO 22
<211> LENGTH: 8
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Dbu
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(8)
<223> OTHER INFORMATION: Bridge
<220> FEATURE:
<221> NAME/KEY: MOD_RES
<222> LOCATION: (4)..(4)
<223> OTHER INFORMATION: 3-PyAla
<220> FEATURE:
<221> NAME/KEY: MOD_RES
<222> LOCATION: (5)..(5)
<223> OTHER INFORMATION: D form
<220> FEATURE:
<221> NAME/KEY: MOD_RES
<222> LOCATION: (8)..(8)
<223> OTHER INFORMATION: AMIDATION

<400> SEQUENCE: 22

Xaa Xaa Glu Xaa Phe Arg Trp Lys
1               5
```

```
<210> SEQ ID NO 23
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 23

Ala Lys Ala Xaa Glu Xaa Phe Arg Trp Lys
1               5                   10

<210> SEQ ID NO 24
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form 4-iodo
<220> FEATURE:
<221> NAME/KEY: MOD_RES
<222> LOCATION: (7)..(7)
<223> OTHER INFORMATION: AMIDATION

<400> SEQUENCE: 24

Xaa Glu Xaa Phe Arg Trp Lys
1               5

<210> SEQ ID NO 25
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
```

```
<223> OTHER INFORMATION: hex-5-eoyl-Nle
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 25

Xaa Glu Xaa Phe Arg Trp Lys
1               5

<210> SEQ ID NO 26
<211> LENGTH: 12
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 26

Gly Ser Gln His Ser Xaa Glu Xaa Phe Arg Trp Lys
1               5                   10

<210> SEQ ID NO 27
<211> LENGTH: 12
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: HomoArg
<220> FEATURE:
<221> NAME/KEY: MOD_RES
<222> LOCATION: (6)..(6)
<223> OTHER INFORMATION: Nle
```

```
<220> FEATURE:
<221> NAME/KEY: MOD_RES
<222> LOCATION: (7)..(12)
<223> OTHER INFORMATION: Bridge
<220> FEATURE:
<221> NAME/KEY: MOD_RES
<222> LOCATION: (8)..(8)
<223> OTHER INFORMATION: 4Hyp
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 27

Gly Ser Gln Xaa Ser Xaa Glu Xaa Phe Arg Trp Lys
1               5                   10

<210> SEQ ID NO 28
<211> LENGTH: 12
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: Nle
<220> FEATURE:
<221> NAME/KEY: MOD_RES
<222> LOCATION: (7)..(12)
<223> OTHER INFORMATION: Bridge
<220> FEATURE:
<221> NAME/KEY: MOD_RES
<222> LOCATION: (8)..(8)
<223> OTHER INFORMATION: Met(O2)
<220> FEATURE:
<221> NAME/KEY: MOD_RES
<222> LOCATION: (9)..(9)
<223> OTHER INFORMATION: D form
<220> FEATURE:
<221> NAME/KEY: MOD_RES
<222> LOCATION: (12)..(12)
<223> OTHER INFORMATION: AMIDATION

<400> SEQUENCE: 28

Gly Ser Gln His Ser Xaa Glu Met Phe Arg Trp Lys
1               5                   10

<210> SEQ ID NO 29
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Bridge
<220> FEATURE:
```

```
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 29

Xaa Glu Xaa Phe Arg Trp Lys
1               5

<210> SEQ ID NO 30
<211> LENGTH: 7
<212> TYPE: PRT
<213> ORGANISM: Artificial
<220> FEATURE:
<223> OTHER INFORMATION: MT-Ii analogue
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: 2-aminoethyl amide

<400> SEQUENCE: 30

Xaa Glu Xaa Phe Arg Trp Lys
1               5

<210> SEQ ID NO 31
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: Phe(4-amino)
<220> FEATURE:
<221> NAME/KEY: MOD_RES
```

```
<222> LOCATION: (4)..(4)
<223> OTHER INFORMATION: D form Phe(4-chloro)
<220> FEATURE:
<221> NAME/KEY: MOD_RES
<222> LOCATION: (7)..(7)
<223> OTHER INFORMATION: AMIDATION

<400> SEQUENCE: 31

Xaa Asp Phe Phe Arg Trp Lys
1               5

<210> SEQ ID NO 32
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 32

Asn Tyr Ser Xaa Glu Xaa Phe Arg Trp Lys
1               5                   10

<210> SEQ ID NO 33
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
```

```
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 33

Ser His Ser Xaa Glu Xaa Phe Arg Trp Lys
1               5                   10

<210> SEQ ID NO 34
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 34

Gln Arg Ser Xaa Glu Xaa Phe Arg Trp Lys
1               5                   10

<210> SEQ ID NO 35
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Homo-Arg
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
```

```
<220> FEATURE:
<221> NAME/KEY: MOD_RES
<222> LOCATION: (10)..(10)
<223> OTHER INFORMATION: AMIDATION

<400> SEQUENCE: 35

Ser Xaa Ser Xaa Glu Xaa Phe Arg Trp Lys
1               5                   10

<210> SEQ ID NO 36
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: Homo-Arg
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 36

Gln Xaa Ser Xaa Glu Xaa Phe Arg Trp Lys
1               5                   10

<210> SEQ ID NO 37
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
```

```
<221> NAME/KEY: MOD_RES
<222> LOCATION: (10)..(10)
<223> OTHER INFORMATION: AMIDATION

<400> SEQUENCE: 37

Ser Asn Ser Xaa Glu Xaa Phe Arg Trp Lys
1               5                   10

<210> SEQ ID NO 38
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 38

Ser Asn Ser Xaa Glu Xaa Phe Arg Trp Lys
1               5                   10

<210> SEQ ID NO 39
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
```

```
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 39

Ser Tyr Xaa Xaa Glu Xaa Phe Arg Trp Lys
1               5                   10

<210> SEQ ID NO 40
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 40

Ser Tyr Xaa Xaa Glu Xaa Phe Arg Trp Lys
1               5                   10

<210> SEQ ID NO 41
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
```

```
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 41

Ser His Xaa Xaa Glu Xaa Phe Arg Trp Lys
1               5                   10

<210> SEQ ID NO 42
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 42

Gln His Xaa Xaa Glu Xaa Phe Arg Trp Lys
1               5                   10

<210> SEQ ID NO 43
<211> LENGTH: 12
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
```

```
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 43

Gln Arg Xaa Xaa Xaa Xaa Glu Xaa Phe Arg Trp Lys
1               5                   10

<210> SEQ ID NO 44
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 44

Asn Arg Xaa Xaa Glu Xaa Phe Arg Trp Lys
1               5                   10

<210> SEQ ID NO 45
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: HomoArg
<220> FEATURE:
```

```
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 45

Asn Xaa Xaa Xaa Glu Xaa Phe Arg Trp Lys
1               5                   10

<210> SEQ ID NO 46
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: 4Hyp
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 46

Ser Asn Xaa Xaa Glu Xaa Phe Arg Trp Lys
1               5                   10

<210> SEQ ID NO 47
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 47

Gln Tyr Pro Xaa Glu Xaa Phe Arg Trp Lys
1               5                   10

<210> SEQ ID NO 48
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 48

Ser His Pro Xaa Glu Xaa Phe Arg Trp Lys
1               5                   10

<210> SEQ ID NO 49
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
```

```
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 49

Asn His Pro Xaa Glu Xaa Phe Arg Trp Lys
1               5                   10

<210> SEQ ID NO 50
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 50

Ser Arg Pro Xaa Glu Xaa Phe Arg Trp Lys
1               5                   10

<210> SEQ ID NO 51
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (4)..(4)
<223> OTHER INFORMATION: Nle
```

```
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 51

Ser Arg Pro Xaa Glu Xaa Phe Arg Trp Lys
1               5                   10

<210> SEQ ID NO 52
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: HomoArg
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 52

Ser Xaa Pro Xaa Glu Xaa Phe Arg Trp Lys
1               5                   10

<210> SEQ ID NO 53
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
```

```
<221> NAME/KEY: MOD_RES
<222> LOCATION: (2)..(2)
<223> OTHER INFORMATION: HomoArg
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 53

Ser Xaa Pro Xaa Glu Xaa Phe Arg Trp Lys
1               5                   10

<210> SEQ ID NO 54
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 54

Gln Asn Pro Xaa Glu Xaa Phe Arg Trp Lys
1               5                   10

<210> SEQ ID NO 55
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
```

<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 55

Asn Asn Pro Xaa Glu Xaa Phe Arg Trp Lys
1               5                   10

<210> SEQ ID NO 56
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 56

Ser Tyr Thr Xaa Glu Xaa Phe Arg Trp Lys
1               5                   10

<210> SEQ ID NO 57
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (4)..(4)

```
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 57

Ser His Thr Xaa Glu Xaa Phe Arg Trp Lys
1               5                   10

<210> SEQ ID NO 58
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 58

Gln His Thr Xaa Glu Xaa Phe Arg Trp Lys
1               5                   10

<210> SEQ ID NO 59
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
```

-continued

```
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 59

Ser Arg Thr Xaa Glu Xaa Phe Arg Trp Lys
1               5                   10

<210> SEQ ID NO 60
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 60

Ser Arg Thr Xaa Glu Xaa Phe Arg Trp Lys
1               5                   10

<210> SEQ ID NO 61
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: HomoArg
<220> FEATURE:
<221> NAME/KEY: MOD_RES
<222> LOCATION: (4)..(4)
<223> OTHER INFORMATION: Nle
<220> FEATURE:
```

```
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 61

Ser Xaa Thr Xaa Glu Xaa Phe Arg Trp Lys
1               5                   10

<210> SEQ ID NO 62
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: HomoArg
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 62

Asn Xaa Thr Xaa Glu Xaa Phe Arg Trp Lys
1               5                   10

<210> SEQ ID NO 63
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
```

```
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 63

Gln Asn Thr Xaa Glu Xaa Phe Arg Trp Lys
1               5                   10

<210> SEQ ID NO 64
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 64

Asn Asn Thr Xaa Glu Xaa Phe Arg Trp Lys
1               5                   10

<210> SEQ ID NO 65
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
```

```
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 65

Ser Tyr Gly Xaa Glu Xaa Phe Arg Trp Lys
1               5                   10

<210> SEQ ID NO 66
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 66

Gln Tyr Gly Xaa Glu Xaa Phe Arg Trp Lys
1               5                   10

<210> SEQ ID NO 67
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
```

```
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 67

Ser His Gly Xaa Glu Xaa Phe Arg Trp Lys
1               5                   10

<210> SEQ ID NO 68
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 68

Asn His Gly Xaa Glu Xaa Phe Arg Trp Lys
1               5                   10

<210> SEQ ID NO 69
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
```

```
<221> NAME/KEY: MOD_RES
<222> LOCATION: (10)..(10)
<223> OTHER INFORMATION: AMIDATION

<400> SEQUENCE: 69

Ser Arg Gly Xaa Glu Xaa Phe Arg Trp Lys
1               5                   10

<210> SEQ ID NO 70
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 70

Asn Arg Gly Xaa Glu Xaa Phe Arg Trp Lys
1               5                   10

<210> SEQ ID NO 71
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: D form
<220> FEATURE:
<221> NAME/KEY: MOD_RES
<222> LOCATION: (2)..(2)
<223> OTHER INFORMATION: HomoArg
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
```

```
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 71

Ser Xaa Gly Xaa Glu Xaa Phe Arg Trp Lys
1               5                   10

<210> SEQ ID NO 72
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: HomoArg
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 72

Gln Xaa Gly Xaa Glu Xaa Phe Arg Trp Lys
1               5                   10

<210> SEQ ID NO 73
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
```

```
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 73

Ser Asn Gly Xaa Glu Xaa Phe Arg Trp Lys
1               5                   10

<210> SEQ ID NO 74
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 74

Ser Tyr Ser Xaa Glu Xaa Phe Arg Trp Lys
1               5                   10

<210> SEQ ID NO 75
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION
```

```
<400> SEQUENCE: 75

Ser His Ser Xaa Glu Xaa Phe Arg Trp Lys
1               5                   10

<210> SEQ ID NO 76
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 76

Ser Arg Ser Xaa Glu Xaa Phe Arg Trp Lys
1               5                   10

<210> SEQ ID NO 77
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 77

Ser His Ser Xaa Asp Xaa Phe Arg Trp Lys
1               5                   10
```

```
<210> SEQ ID NO 78
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 78

Ser His Ser Xaa Glu Ser Phe Arg Trp Lys
1               5                   10

<210> SEQ ID NO 79
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (7)..(7)
<223> OTHER INFORMATION: D form Phe(3-trifluoromethyl)
<220> FEATURE:
<221> NAME/KEY: MOD_RES
<222> LOCATION: (10)..(10)
<223> OTHER INFORMATION: AMIDATION

<400> SEQUENCE: 79

Ser His Ser Xaa Glu Xaa Phe Arg Trp Lys
1               5                   10

<210> SEQ ID NO 80
<211> LENGTH: 10
<212> TYPE: PRT
```

```
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (7)..(7)
<223> OTHER INFORMATION: D form Phe(2-methyl)
<220> FEATURE:
<221> NAME/KEY: MOD_RES
<222> LOCATION: (7)..(7)
<223> OTHER INFORMATION: D form Phe(2-methyl)
<220> FEATURE:
<221> NAME/KEY: MOD_RES
<222> LOCATION: (10)..(10)
<223> OTHER INFORMATION: AMIDATION

<400> SEQUENCE: 80

Ser His Ser Xaa Glu Xaa Phe Arg Trp Lys
1               5                   10

<210> SEQ ID NO 81
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: 4Hyp
<220> FEATURE:
<221> NAME/KEY: MOD_RES
<222> LOCATION: (7)..(7)
<223> OTHER INFORMATION: D form Phe(2-chloro)
<220> FEATURE:
<221> NAME/KEY: MOD_RES
<222> LOCATION: (10)..(10)
<223> OTHER INFORMATION: AMIDATION

<400> SEQUENCE: 81

Ser Glu Ser Xaa Glu Xaa Phe Arg Trp Lys
1               5                   10

<210> SEQ ID NO 82
<211> LENGTH: 7
<212> TYPE: PRT
<213> ORGANISM: Artificial
```

-continued

```
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 82

Xaa Asp Thr Phe Arg Trp Lys
1               5

<210> SEQ ID NO 83
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: 2,3-diamino propionic acid
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 83

Xaa Asp Xaa Phe Arg Trp Lys
1               5

<210> SEQ ID NO 84
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
```

```
<223> OTHER INFORMATION: Bridge
<220> FEATURE:
<221> NAME/KEY: MOD_RES
<222> LOCATION: (3)..(3)
<223> OTHER INFORMATION: Ala(4-thiazolyl)
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 84

Xaa Asp Xaa Phe Arg Trp Lys
1               5

<210> SEQ ID NO 85
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: Phe(4-amino)
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 85

Xaa Asp Phe Phe Arg Trp Lys
1               5

<210> SEQ ID NO 86
<211> LENGTH: 7
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(7)
<223> OTHER INFORMATION: Bridge
<220> FEATURE:
<221> NAME/KEY: MOD_RES
<222> LOCATION: (3)..(3)
<223> OTHER INFORMATION: citrulline
```

```
<220> FEATURE:
<221> NAME/KEY: MOD_RES
<222> LOCATION: (4)..(4)
<223> OTHER INFORMATION: D form
<220> FEATURE:
<221> NAME/KEY: MOD_RES
<222> LOCATION: (7)..(7)
<223> OTHER INFORMATION: AMIDATION

<400> SEQUENCE: 86

Xaa Asp Xaa Phe Arg Trp Lys
1               5

<210> SEQ ID NO 87
<211> LENGTH: 10
<212> TYPE: PRT
<213> ORGANISM: Artificial
<220> FEATURE:
<223> OTHER INFORMATION: MT-II analogue
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (5)..(10)
<223> OTHER INFORMATION: Bridge
<220> FEATURE:
<221> NAME/KEY: MOD_RES
<222> LOCATION: (6)..(6)
<223> OTHER INFORMATION: Ala(4-thiazolyl)
<220> FEATURE:
<221> NAME/KEY: MOD_RES
<222> LOCATION: (7)..(7)
<223> OTHER INFORMATION: D form
<220> FEATURE:
<221> NAME/KEY: MOD_RES
<222> LOCATION: (10)..(10)
<223> OTHER INFORMATION: AMIDATION

<400> SEQUENCE: 87

Ser His Ser Xaa Asp Xaa Phe Arg Trp Lys
1               5                   10
```